(12) United States Patent
Hans et al.

(10) Patent No.: US 9,315,784 B2
(45) Date of Patent: Apr. 19, 2016

(54) MODIFIED TRANSKETOLASE AND USE THEREOF

(75) Inventors: Michael Hans, Schopfheim (DE); Dietmar Laudert, Schopfheim (DE); Hans-Peter Hohmann, Loerrach (DE); Martin Lehmann, Grenzach-Wyhlen (DE)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/558,517

(22) Filed: Jul. 26, 2012

(65) Prior Publication Data

US 2013/0189731 A1 Jul. 25, 2013

Related U.S. Application Data

(63) Continuation of application No. 12/091,279, filed as application No. PCT/EP2006/010270 on Oct. 25, 2006, now Pat. No. 8,257,944.

(30) Foreign Application Priority Data

Nov. 2, 2005 (EP) ..................................... 05023813

(51) Int. Cl.
| | |
|---|---|
| C12P 17/18 | (2006.01) |
| C12N 9/10 | (2006.01) |
| C12P 25/00 | (2006.01) |
| C12P 17/12 | (2006.01) |

(52) U.S. Cl.
CPC ............... *C12N 9/1022* (2013.01); *C12P 17/12* (2013.01); *C12P 25/00* (2013.01)

(58) Field of Classification Search
IPC ............... C12P 17/182; C12N 9/1022
See application file for complete search history.

(56) References Cited

FOREIGN PATENT DOCUMENTS

EP 0 969 096 1/2000

OTHER PUBLICATIONS

Nilsson et al. "Examination of substrate binding in thiamin diphosphate-dependent transketolase by protein crystallography and site-directed mutagenesis" J. Biol. Chem., vol. 272, No. 3, pp. 1864-1869 (1997).
Soh et al. "Critical role of Arg433 in rat transketolase activity as probed by site-directed mutagenesis" Biochem. J., vol. 333, No. 2, pp. 367-372 (Jul. 15, 1998).
De Wulf et al. "Production of D-ribose by fermentation" Appl. Microbiol. Biotech. vol. 48, No. 2, pp. 141-148 (1997).
International Search Report for PCT/EP2006/010270, mailed Apr. 17, 2007.
Written Opinion of the International Searching Authority, mailed Apr. 17, 2007.

(Continued)

*Primary Examiner* — Rosanne Kosson
(74) *Attorney, Agent, or Firm* — Nixon & Vanderhye P.C.

(57) ABSTRACT

The present invention relates to a improved process for the biotechnological production of compounds for which ribose-5-phosphate, ribulose-5-phosphate or xylulose-5-phosphate is biosynthetic precursor like riboflavin (vitamin $B_2$), FAD, FMN, pyridoxal phosphate (vitamin $B_6$), guanosine, GMP, adenosine, AMP. The invention further pertains to the generation of the organism producing those compounds. It furthermore relates to the generation of mutated transketolases that allow normal growth on glucose but reduced growth on gluconate when introduced into the production strains and to polynucleotides encoding them.

6 Claims, 4 Drawing Sheets

(56) References Cited

OTHER PUBLICATIONS

Park, et al; "Optimization of culture conditions for d-ribose production by transketolase-deficient Bacillus subtilis JY1," J. Microbiol. Biotechnol. vol. 14, No. 4, pp. 665-672 (2004).

Gershanovich et al; "Transketolase mutation in riboflavin-producing strains of Bacillus subtilis," Molekularnaya Genetika, Mikrobiologiya I Virusologiya, vol. 2000, No. 3, pp. 3-7 (2000), in Russian.

Gershanovich et al; "Transketolase mutation in riboflavin-producing strains of Bacillus subtilis," Molekularnaya Genetika, Mikrobiologiya I Virusologiya, vol. 2000, No. 3, pp. 3-7 (2000), English translation.

GenBank Record No. 1NGS_A, Protein database record for transketolase from *Saccharomyces cerevisiae*, The Transketolase of Nilsson et al, printed on Apr. 15, 2010.

Blast2 alignment of instant SEQ ID No. 2 with the transketolase sequence of Nilsson et al, GenBank Record No. 1NGS_A, performed on the NCBI Blast website, http://blast.ncbi.nlm.nih.gov/Blast.cgi, on Apr. 15, 2010.

Molasses Composition, United States Sugar Corporation, Molasses & Liquid Feeds Div., http://www.suga-lik.com/molasses/composition.html, 2003.

Figure 1:

TKT_ECOLI: *Escherichia coli*
TKT_BACSU: *Bacillus subtilis*
TKT_BACLD: *Bacillus licheniformis*
TKT_BACHD: *Bacillus halodurans*
TKT_CORGL: *Corynebacterium glutamicum*
TKT_YEAST: *Saccharomyces cerevisiae*
TKT_ASHGO: *Ashbya gossypii*

CLUSTAL W (1.83) multiple sequence alignment

```
TKT1_ECOLI   ------------------------------MSSRKELANAIRALSMDAVQKAKSGHPGAPMGMADIAE
TKT2_ECOLI   ------------------------------MSRKDLANAIRALSMDAVQKANSGHPGAPMGMADIAE
TKT_BACSU    ----------------------------MDTIEKKSVATIRTLSIDAIEKANSGHPGMPMGAAPMAY
TKT_BACLD    ----------------------------MKTIELKSVATIRTLSIDAIEKAKSGHPGMPMGTAPMAY
TKT_BACHD    ----------------------------MSKHVEQLAVNTIRTLSIDSVEKANSGHPGMPMGAAPMAF
TKT_CORGL    MTTLTLSPELQALTVRNYPSDWSDVDTKAVDTVRVLAADAVENCGSGHPGTAMSLAPLAY
TKT1_YEAST   --------------------TQFTDIDKLAVSTIRILAVDTVSKANSGHPGAPLGMAPAAH
TKT_ASHGO    ------------------MTQFSDVDRLAVSTIRLLSVDQVSKANSGHPGAPLGLAPAAH
TKT2_YEAST   ------------------MAQFSDIDKLAVSTIRLLSVDQVESAQSGHPGAPLGLAPVAH

TKT1_ECOLI   VLWRDFLKHNPQNPSWADRDRFVLSNGHGSMLIYSLLHLTGYDLPMEELKNFRQLHSKTP
TKT2_ECOLI   VLWNDFLKHNPTDPTWYDRDRFILSNGHASMLLYSLLHLTGYDLPLEELKNFRQLHSKTP
TKT_BACSU    TLWTKFMNVSPANPGWFNRDRFVLSAGHGSALLYSMLRLSGFDLSIEDLKGFRQWGSKTP
TKT_BACLD    ALWTKMMNVSPENPNWFNRDRFVLSAGHGSMLLYSMLHLSGYDVSIEDLKNFRQWGSKTP
TKT_BACHD    CLWTKFMNHNPANPDWVNRDRFVLSAGHGSMLLYSLLHLTGYDLSLEELQNFRQWGSKTP
TKT_CORGL    TLYQRVMNVDPQDFNWAGRDRFVLSCGHSSLTQYIQLYLGGFGLEMDDLKALRTWDSLTP
TKT1_YEAST   VLWSQMR-MNFTNPDWINRDRFVLSNGHAVALLYSMLHLTGYDLSIEDLKQFRQLGSRTP
TKT_ASHGO    VVWKQMR-LNPKSPKWINRDRFVLSNGHACALLYSLLHLFGYDLSIEDLKQFRQVGSKTP
TKT2_YEAST   VIFKQLR-CNPNNERWINRDRFVLSNGHSCALLYSMLHLLGYDYSIEDLRQFRQVNSRTP

TKT1_ECOLI   GHPEVGYTAGVETTTGPLGQGIANAVGMAIAEKTLAAQFN---RPGHDIVDHYTYAFMGD
TKT2_ECOLI   GHPEIGYTPGVETTTGPLGQGLANAVGLAIAERTLAAQFN---QPDHEIVDHFTYVFMGD
TKT_BACSU    GHPEFGHTAGVDATTGPLGQGIAMAVGMAIAERHLAETYN---RDSFNVVDHYTYSICGD
TKT_BACLD    GHPEFGHTPGVDATTGPLGQGIGMAVGMAIAERHLAETYN---RDDYRVVDHYTYSICGD
TKT_BACHD    GHPEYGHTPGVEATTGPLGQGVAMAVGMAMAERHLAATYN---RDGYNIVDHYTYTICGD
TKT_CORGL    GHPEYRHTKGVEIFTGPLGQGLASAVGMAMAARKERGLFDPTAAEGESPFDHHIYVIASD
TKT1_YEAST   GHPEF-ELPGVEVTTGPLGQGISNAVGMAMAQANLAATYN---KPGFTLSDNYTYVFLGD
TKT_ASHGO    GHPEY-ELPGVEVTTGPLGQGISNAVGLAIAQANLAATYN---KPGYELSDNYTYVFLGD
TKT2_YEAST   GHPEF-HSAGVEITSGPLGQGISNAVGMAIAQANFAATYN---EDGFPISDSYTFAIVGD

TKT1_ECOLI   GCMMEGISHEVCSLAGTLKLGKLIAFYDDNGISIDGHVEGWFTDDTAMRFEAYGWHVIRD
TKT2_ECOLI   GCLMEGISHEVCSLAGTLGLGKLIGFYDHNGISIDGETEGWFTDDTAKRFEAYHWHVIHE
TKT_BACSU    GDLMEGISSEAASLAGHLQLGRLIVLYDSNDISLDGDLDRSFSENVKQRFEAMNWEVLYV
TKT_BACLD    GDLMEGISSEAASLAGHLNLGRLIVLYDSNDISLDGELNRSFSENVKQRFEAMNWEVLYV
TKT_BACHD    GDLMEGVSAEAASLAGHLKLGRMILLYDSNDISLDGDLHHSFSESVEDRFKAYGWHVVRV
TKT_CORGL    GDLQEGVTSEASSIAGTQQLGNLIVFWDDNRISIEDNTEIAFNEDVVARYKAYGWQTIEV
TKT1_YEAST   GCLQEGISSEASSLAGHLKLGNLIAIYDDNKITIDGATSISFDEDVAKRYEAYGWEVLYV
TKT_ASHGO    GCLQEGVSSEASSLAGHLKLGNLIAFYDDNKITIDGHTEVSFDEDVLKRYEAYGWEVLNV
TKT2_YEAST   GCLQEGVSSETSSLAGHLQLGNLITFYDSNSISIDGKTSYSFDEDVLKRYEAYGWEVMEV
```

Figure 1: Continued

```
TKT1_ECOLI  IDGH-DAASIKPAVEEARAVTDKPSLLMCKTIIGFGSPNKAGTHDSHGAPLGDAEIALTR
TKT2_ECOLI  IDGH-DPQAVKEAILEAQSVKDKPSLIICRTVIGFGSPNKAGKEEAHGAPLGEEEVALAR
TKT_BACSU   EDGN-NIEELTAAIEKARQNEKKPTLIEVKFTIGFGSPNRAGTSGVHGAPLGKEESKLTK
TKT_BACLD   EDGN-NIAEITAAIEKAKQNEKQPTLIEVKFTIGFGSPNRAGTSGVHGAPLGSEEAKLTK
TKT_BACHD   EDGN-NLDEIAKAIEEAKADER-PSLIEVKFTIGFGSPNKGGKSVSHGAPLGADEVKLTK
TKT_CORGL   EAGE-DVAAIEAAVAEAKKDTKRPTFIRVRTIIGFPAPTMMNTGAVHGAALGAAEVAATK
TKT1_YEAST  ENGNEDLAGIAKAIAQAKLSKDKPTLIKMTTTIGYGSLH-AGSHSVHGAPLKADDVKQLK
TKT_ASHGO   ANGDENLEDIASALEQAKKNKDKPTLIKLTTTIGFGSLN-AGSHTVHGAPLKADDVKQLK
TKT2_YEAST  DKGDDDMESISSALEKAKLSKDKPTIIKVTTTIGFGSLQ-QGTAGVHGSALKADDVKQLK

TKT1_ECOLI  EQLGWKYAP-FEIPSEIYAQW--DAKEAGQAKESAWNEKFAAYAKAYPQEAAEFTRRMKG
TKT2_ECOLI  QKLGWHSPP-FEIPKEIYHAW--DAREKGEKAQQSWNEKFAAYKKAHPQLAEEFTRRMSG
TKT_BACSU   EAYAWTYEEDFYVPSEVYEHFAVAVKESGEKKEQEWNAQFAKYKEVYPELAEQLELAIKG
TKT_BACLD   EAYEWTYEEDFYVPSEVYEHFNETVKEAGKKKEAEWNELFSAYKKAHPELAEELELAIKG
TKT_BACHD   EAYEWTYENEFHIPEEVAAYY-EQVKQQGAEKEESWNELFAQYKKAYPELASQFELAVHG
TKT_CORGL   TELGFDPEAHFAIDDEVIAHT-RSLAERAAQKKAAWQVKFDEWAAANPENKAIFDRLNSR
TKT1_YEAST  SKFGFNPDKSFVVPQEVYDHYQKTILKPGVEANNKWNKLFSEYQKKFPELGAELARRLSG
TKT_ASHGO   TKLGFNPDESFIVPQEVYDLYHNSTIQPGAESEKEWNALLEKYAGEYPKEAAELKRRLAG
TKT2_YEAST  KRWGFDPNKSFVVPQEVYDYYKKTVVEPGQKLNEEWDRMFEEYKTKFPEKGKELQRRLNG

"357"
TKT1_ECOLI  EMPSDFDAKAKEFIAKLQANPAKIASRKASQNAIEAFGPLLPEFLGGSADLAPSNLTLWS
TKT2_ECOLI  GLPKDWEKTTQKYINELQANPAKIATRKASQNFLNAYGPMLPELLGGSADLAPSNLTIWK
TKT_BACSU   ELPKDWDQEVP-----VYEKG-SSLASKASSGEVLNGLAKKIPFFVGGSADLAGSNKTTIK
TKT_BACLD   ELPKDGWDQKVP-----VYEKG-SSLASKASSGEVLNGIAQQVPFFPGGSADLAGSNKTTIK
TKT_BACHD   DLPEGWDAVAP-----SYEVG-KSVATPSSSGEALNAFAKTVPQLFGGSADLASSNKTLIK
TKT_CORGL   ELPAGYADELP-----TWDADENGVATRKASEAALQALGKTLPELWGGSADLAGSNNTVIK
TKT1_YEAST  QLPANWESKLP-----TYTAKDSAVATRKLSETVLEDVYNQLPELIGGSADLTPSNLTRWK
TKT_ASHGO   KLPENWESKLP-----VYKPTDSAVASRKLSEIVLQSIFEDVPELIGGSADLTPSNLTKTT
TKT2_YEAST  ELPEGWEKHLP-----KFTPDDDALATRKTSQQVLTNMVQVLPELIGGSADLTPSNLTRWE

TKT1_ECOLI  GSKAINEDAAG------------NYIHYGVREFGMTAIANGISLHGG-FLPYTSTFLMFVEY
TKT2_ECOLI  GSVSLKEDPAG------------NYIHYGVREFGMTAIANGIAHHGG-FVPYTATFLNFVEY
TKT_BACSU   NAGDFTAVDYS-----------GKNFWFGVREFAMGAALNGMALHGG-LRVFGGTFFVFSDY
TKT_BACLD   NGGDVSAKDYA-----------GKNIWFGVREFAMGAALNGMALHGG-LRVFGGTFFVFSDY
TKT_BACHD   GEANFSRDDYS-----------GRNVWFGVREFAMGAAMNGMALHGG-LKVFGATFFVFSDY
TKT_CORGL   GSPSFGPESISTETWSAEPYGRNLRFGIREHAMGSILNGISLHGG-TRPYGGTFLIFSDY
TKT1_YEAST  EALDFQPPSSG----SGNYSGRYIRYGIREHAMGAIMNGISAFGANYKPYGGTFLNFVSY
TKT_ASHGO   NAVDFQPPQSG------LGDYSGRYIRFGVREHGMGAIINGLSAYGANYKVFGATFLNFVSY
TKT2_YEAST  GAVDFQPPITQ----LGNYAGRYIRYGVREHGMGAIMNGISAFGANYKPYGGTFLNFVSY

TKT1_ECOLI  ARNAVRMAALMKQRQVMVYTHDSIGLGEDGPTHQPVEQVASLRVTPNMSTWRPCDQVESA
TKT2_ECOLI  ARNAARMAALMKARQIMVYTHDSIGLGEDGPTHQAVEQLASLRLTPNFSTWRPCDQVEAA
TKT_BACSU   LRPAIRLAALMGLPVTYVFTHDSIAVGEDGPTHEPVEQLASLRAMPNLSLIRPADGNETA
TKT_BACLD   LRPAIRLAALMGLPVTYVFTHDSIAVGEDGPTHEPIEQLASLRALPNLSVIRPADGNETA
TKT_BACHD   LRPAIRLAALMQLPVIYVFTHDSIAVGEDGPTHEPVEQLASLRAMPGLSVIRPADGNESV
TKT_CORGL   MRPAVRLAALMETDAYYVWTHDSIGLGEDGPTHQPVETLAALRAIPGLSVLRPADANETA
TKT1_YEAST  AAGAVRLSALSGHPVIWVATHDSIGVGEDGPTHQPIETLAHFRSLPNIQVWRPADGNEVS
TKT_ASHGO   AAGAVRLAALSGHPVIWIATHDSIGLGEDGPTHQPIETLAHLRAIPNMMVWRPADGNEVS
TKT2_YEAST  AAGAVRLAALSGNPVIWVATHDSIGLGEDGPTHQPIETLAHLRAIPNMHVWRPADGNETS
```

Figure 1: Continued

```
TKT1_ECOLI    VAWKYGVERQDGPTALILSRQNLAQQERTEEQLAN-IARGGYVLKD-CAGQPELIFIATG
TKT2_ECOLI    VGWKLAVERHNGPTALILSRQNLAQVERTPDQVKE-IARGGYVLKD-SGGKPDIILIATG
TKT_BACSU     AAWKLAVQSTDHPTALVLTRQNLPTIDQTSEEALAGVEKGAYVVSKSKNETPDALLIASG
TKT_BACLD     AAWKLALQSKDQPTALVLTRQNLPTIDQSAETAYEGVRKGAYVVSKSQNEKPEATLLASG
TKT_BACHD     AAWKLALESEDQPTALVLSRQNLPTLEGAVDRAYDGVSRGAYVLAP-ANGSADLLLLASG
TKT_CORGL     QAWAAALEYKEGPKGLALTRQNVPVLEGTKEKAAEGVRRGGYVLVEGSKETPDVILMGSG
TKT1_YEAST    AAYKNSLESKHTPSIIALSRQNLPQLEGSSIESAS---KGGYVLQD--VANPDIILVATG
TKT_ASHGO     AAYKVALESQDTPSVIALSRQNLPQLDGSSIEKAS---KGGYILQD--VENPDIAIVSTG
TKT2_YEAST    AAYYSAIKSGPTPSVVALSRQNLPQLEHSSFEKAL---KGGYIHD--VENPDIILVSTG

TKT1_ECOLI    SEVELAVAAYEKLTA-EGVKARVVSMPSTDAFDKQDAAYRESVLPKAVTARVAVEAGIAD
TKT2_ECOLI    SEMEITLQAAEKLAG-EGRNVRVVSLPSTDIFDAQDEEYRESVLPSNVAARVAVEAGIAD
TKT_BACSU     SEVGLAIEAQAELAK-ENIDVSVVSMPSMDPFEKQSDEYKNEVLPADVKKRLAIEMGSSF
TKT_BACLD     SEVGLALDAQSELQK-EGIDVSVVSVPSWDRFDKQPAEYKNAVLPTDVTKRLAIEMGSPL
TKT_BACHD     SEVSIAVNAKEALEK-EGIHAAVVSMPSWDRPEAQSAEYKEEVLPSDVTARLAIEMGSSL
TKT_CORGL     SEVQLAVNAAKALEA-EGVAARVVSVPCMDWFQEQDAEYIESVLPAAVTARVSVEAGIAM
TKT1_YEAST    SEVSLSVEAAKTLAA-KNIKARVVSLPDFFTFDKQPLEYRLSVLPDNVP-IMSVEVLATT
TKT_ASHGO     SEVGIAVEAAKILAE-KNMKVRIVSLPDFHTFSRQPKEYQLSVLPDRVP-ILSVEVLSTS
TKT2_YEAST    SEVSISIDAAKKLYDTKKIKARVVSLPDFYTFDRQSEEYRPSVLPDGVP-IMSFEVLATS

TKT1_ECOLI    YWYKYVGLNGAIVGMTTFGESAPAELLFEEFGFTVDNVVARAKELL---------------
TKT2_ECOLI    YWYKYVGLKGAIVGMTGYGESAPADKLFPPFGFTAENIVARAHKVLGVKGA----------
TKT_BACSU     GWGKYTGLEGDVLGIDRFGASAPGETIINEYGFSVPNVVNRVKALINK-------------
TKT_BACLD     GWERYTGTDGDILGIDQFGASAPGEFIMKEYGFTPANVVDRVKKLLNR-------------
TKT_BACHD     GWAKYVGNQGDVVAIDRFSASAPGERIMEEFGFTVQHVVARAKALLENK------------
TKT_CORGL     PWYRFLGTQGRAVSLEHPGASADYQTLFEKFGIFTDAVVAAAKDSING-------------
TKT1_YEAST    CWGKYAHQS---FGIDRFGASGKAPEVFKFFGFTPEGVAERAQKTIAFYKGDKLISPLKK
TKT_ASHGO     GWSRYAHQS---FGLNRFGASGKGPEVYKFFEFTPEGIASRAEKTVAFYKGKEVLSPLNK
TKT2_YEAST    SWGKYAHQS---FGLDEFGRSGKGPEIYKLFDFTADGVASRAEKTINYYKGKQLLSPMGR

TKT1_ECOLI    --
TKT2_ECOLI    --
TKT_BACSU     --
TKT_BACLD     --
TKT_BACHD     --
TKT_CORGL     --
TKT1_YEAST    AF
TKT_ASHGO     AF
TKT2_YEAST    AF
```

Figure 2:

tkt 1S: 5'-aggagaaatcatatggatacaattgaaaagaaatcag-3'
tkt 1AS: 5'-aattaaatggatccttacttattgattaatgccttaac-3'
tkt 1ASohne: 5'-aattaaatggatcccttattgattaatgccttaac-3'
tkt 2S: 5'-ggacatactgccggtgttgatg-3'
tkt 2AS: 5'-ggacatactgccggtgttgatg-3'
tkt 3S: 5'-ttgaagaattaacagcggc-3'
tkt 4S: 5'-cagcttgaactggcaatc-3'
tkt 5S: 5'-gtcctgcgattcgccttg-3'
tkt 6S: 5'-acgaaacacccgacgctc-3'
tkt 357 AS: 5'-ggatgccaaactgcttcc-3'
tkt Rec 1S: 5'-ggggcagcaaaacaccaggac-3'
tkt Rec 1AS: 5'-gatctcgaccctgcagcccaagcacacaggaacctcttgatccc-3'
tkt Rec 2S: 5'-gcgtcaaaacgcataccattttgaacaaaaccttcctaccatcgatc-3'
tkt Rec 2AS: 5'-cttattgattaatgccttaactcg-3'
tkt 357A-S: 5'-agcagtttggcatccgcagcatcttccggtgaagttc-3'
tkt 357N-S: 5'-agcagtttggcatccaacgcatcttccggtgaagttc-3'
tkt 357K-S: 5'-agcagtttggcatccaaagcatcttccggtgaagttc-3'
tkt 357Q-S: 5'-agcagtttggcatcccaagcatcttccggtgaagttc-3'
tkt 357S-S: 5'-agcagtttggcatcctcagcatcttccggtgaagttc-3'
tkt 357T-S: 5'-agcagtttggcatccacagcatcttccggtgaagttc-3'
tkt 357H-S: 5'-agcagtttggcatcccatgcatcttccggtgaagttc-3'
tkt 357V-S: 5'-agcagtttggcatccgtggcatcttccggtgaagttc-3'
tkt 357I-S: 5'-agcagtttggcatccattgcatcttccggtgaagttc-3'
tkt 357L-S: 5'-agcagtttggcatccttggcatcttccggtgaagttc-3'
tkt 357M-S: 5'-agcagtttggcatccatggcatcttccggtgaagttc-3'
tkt 357G-S: 5'-agcagtttggcatccggtgcatcttccggtgaagttc-3'
rpi MutS: 5'-aattaaatgaattcattaaagaggagaaatcatatg-3'

SEQUENCE LISTING

<160> NUMBER OF SEQ ID NOS: 40

<210> SEQ ID NO 1
<211> LENGTH: 2004
<212> TYPE: DNA
<213> ORGANISM: Bacillus sp.

<400> SEQUENCE: 1

```
atggatacaa ttgaaaagaa atcagttgct accattcgca cactgtcaat agacgctatt    60
gaaaaagcaa attctggtca cccagggatg ccgatgggag ccgctccaat ggcatacacg   120
ctgtggacaa aatttatgaa cgtaagtccg gcaaaccctg gctggtttaa ccgtgaccgt   180
tttgttttat ctgctggaca cgggtcagca ctattataca gcatgcttca tttaagcggg   240
tttgatctta gtattgaaga tcttaaggga ttccgccagt ggggcagcaa acaccagga    300 catccggaat tcggacatac tgccggtgtt gatgctacaa caggtccgct tggccaagga   360
attgccatgg cagtcggtat ggcaattgct gaacgccatt tagcggaaac atacaaccgc   420
gattcattta acgtagtcga tcattataca tacagtattt gcggtgatgg tgatttaatg   480
gaaggtattt cttctgaagc cgcttcactc gcaggccatc ttcagcttgg ccgtctgatc   540
gtactatacg attctaatga catctctctt gatggagacc tcgaccgttc attctctgaa   600
aacgtgaaac agcgttttga agcaatgaat tgggaagttc tttatgttga ggatggaaac   660
aatattgaag aattaacagc ggctatcgaa aaagcacgcc aaaatgaaaa gaaacctaca   720
ttaattgaag tgaaaacgac aatcggattc ggttcaccta accgtgccgg tacatccggt   780
gttcacggtg cgccgcttgg taaagaagaa agcaaattaa caaaagaagc ttacgcgtgg   840
acatatgaag aagacttcta cgttccgtca gaagtttatg agcatttcgc tgtagctgtt   900
aaagaatcag gtgagaaaaa agaacaagaa tggaatgctc aattcgctaa atataaagaa   960
gtttatcctg aacttgctga acagcttgaa ctggcaatca aaggagagct tccgaaggac  1020
tgggatcaag aggttcctgt gtatgaaaaa ggaagcagtt tggcatcccg tgcatcttcc  1080
ggtgaagttc tcaacggact tgcgaaaaaa attccttttct tgtcggagg ttctgctgac  1140 ctagcgggat cgaacaaaac gactattaaa aatgccggtg attttacagc ggttgattac  1200
tcaggcaaaa acttctggtt tggtgtacgt gaatttgcga tgggtgcggc cttaaacggt  1260
atggcgcttc atggcggtct tcgtgtattc ggcggaactt tctttgtctt ctctgattac  1320
ctgcgtcctg cgattcgcct tgcagcgtta atgggccttc ctgtgacata tgtcttcaca  1380
catgacagta ttgcggttgg tgaagacggt ccgacgcacg agcctgttga acagcttgct  1440
```

```
tcactccgtg cgatgcctaa cctttctttg atccgtccag cagacggcaa tgagacagca   1500
gcagcatgga agcttgcagt gcaaagcact gaccacccaa cagcgctagt gcttacacgt   1560
caaaaccttc ctaccatcga tcaaacatct gaagaagcat tggcaggagt agaaaaaggt   1620
gcatatgtcg tttctaaatc taaaaacgaa acacccgacg ctcttctcat cgcttccgga   1680
tcagaggtag gtcttgcaat tgaagcgcag gctgaattgg caaaagaaaa tatcgatgtt   1740
tctgttgtca gcatgccttc aatggaccgt tttgagaaac aatctgatga atacaaaaac   1800
gaagtccttc ctgcagatgt gaaaaaacgt cttgcaattg aaatgggctc atcatttgga   1860
tggggcaaat acacggggct tgaaggtgac gttctcggca tagaccgatt cggtgcatct   1920
gctcctggtg aaaccatcat taacgaatac ggcttctcag ttccgaacgt agtgaatcga   1980
gttaaggcat taatcaataa gtaa                                          2004
```

<210> SEQ ID NO 2
<211> LENGTH: 667
<212> TYPE: PRT
<213> ORGANISM: Bacillus sp.

<400> SEQUENCE: 2

```
Met Asp Thr Ile Glu Lys Lys Ser Val Ala Thr Ile Arg Thr Leu Ser
1               5                   10                  15

Ile Asp Ala Ile Glu Lys Ala Asn Ser Gly His Pro Gly Met Pro Met
            20                  25                  30

Gly Ala Ala Pro Met Ala Tyr Thr Leu Trp Thr Lys Phe Met Asn Val
        35                  40                  45

Ser Pro Ala Asn Pro Gly Trp Phe Asn Arg Asp Arg Phe Val Leu Ser
    50                  55                  60

Ala Gly His Gly Ser Ala Leu Leu Tyr Ser Met Leu His Leu Ser Gly
65                  70                  75                  80

Phe Asp Leu Ser Ile Glu Asp Leu Lys Gly Phe Arg Gln Trp Gly Ser
                85                  90                  95

Lys Thr Pro Gly His Pro Glu Phe Gly His Thr Ala Gly Val Asp Ala
            100                 105                 110

Thr Thr Gly Pro Leu Gly Gln Gly Ile Ala Met Ala Val Gly Met Ala
        115                 120                 125

Ile Ala Glu Arg His Leu Ala Glu Thr Tyr Asn Arg Asp Ser Phe Asn
    130                 135                 140

Val Val Asp His Tyr Thr Tyr Ser Ile Cys Gly Asp Gly Asp Leu Met
145                 150                 155                 160

Glu Gly Ile Ser Ser Glu Ala Ala Ser Leu Ala Gly His Leu Gln Leu
                165                 170                 175

Gly Arg Leu Ile Val Leu Tyr Asp Ser Asn Asp Ile Ser Leu Asp Gly
            180                 185                 190

Asp Leu Asp Arg Ser Phe Ser Glu Asn Val Lys Gln Arg Phe Glu Ala
        195                 200                 205

Met Asn Trp Glu Val Leu Tyr Val Glu Asp Gly Asn Asn Ile Glu Glu
    210                 215                 220

Leu Thr Ala Ala Ile Glu Lys Ala Arg Gln Asn Glu Lys Lys Pro Thr
225                 230                 235                 240

Leu Ile Glu Val Lys Thr Thr Ile Gly Phe Gly Ser Pro Asn Arg Ala
                245                 250                 255

Gly Thr Ser Gly Val His Gly Ala Pro Leu Gly Lys Glu Glu Ser Lys
            260                 265                 270
```

```
Leu Thr Lys Glu Ala Tyr Ala Trp Thr Tyr Glu Glu Asp Phe Tyr Val
        275                 280                 285

Pro Ser Glu Val Tyr Glu His Phe Ala Val Ala Val Lys Glu Ser Gly
290                 295                 300

Glu Lys Glu Gln Glu Trp Asn Ala Gln Phe Ala Lys Tyr Lys Glu
305                 310                 315                 320

Val Tyr Pro Glu Leu Ala Glu Gln Leu Glu Leu Ala Ile Lys Gly Glu
                325                 330                 335

Leu Pro Lys Asp Trp Asp Gln Glu Val Pro Val Tyr Glu Lys Gly Ser
                340                 345                 350

Ser Leu Ala Ser Arg Ala Ser Ser Gly Glu Val Leu Asn Gly Leu Ala
                355                 360                 365

Lys Lys Ile Pro Phe Phe Val Gly Gly Ser Ala Asp Leu Ala Gly Ser
        370                 375                 380

Asn Lys Thr Thr Ile Lys Asn Ala Gly Asp Phe Thr Ala Val Asp Tyr
385                 390                 395                 400

Ser Gly Lys Asn Phe Trp Phe Gly Val Arg Glu Phe Ala Met Gly Ala
                405                 410                 415

Ala Leu Asn Gly Met Ala Leu His Gly Gly Leu Arg Val Phe Gly Gly
                420                 425                 430

Thr Phe Phe Val Phe Ser Asp Tyr Leu Arg Pro Ala Ile Arg Leu Ala
            435                 440                 445

Ala Leu Met Gly Leu Pro Val Thr Tyr Val Phe Thr His Asp Ser Ile
450                 455                 460

Ala Val Gly Glu Asp Gly Pro Thr His Glu Pro Val Glu Gln Leu Ala
465                 470                 475                 480

Ser Leu Arg Ala Met Pro Asn Leu Ser Leu Ile Arg Pro Ala Asp Gly
                485                 490                 495

Asn Glu Thr Ala Ala Ala Trp Lys Leu Ala Val Gln Ser Thr Asp His
                500                 505                 510

Pro Thr Ala Leu Val Leu Thr Arg Gln Asn Leu Pro Thr Ile Asp Gln
            515                 520                 525

Thr Ser Glu Glu Ala Leu Ala Gly Val Glu Lys Gly Ala Tyr Val Val
            530                 535                 540

Ser Lys Ser Lys Asn Glu Thr Pro Asp Ala Leu Leu Ile Ala Ser Gly
545                 550                 555                 560

Ser Glu Val Gly Leu Ala Ile Glu Ala Gln Ala Glu Leu Ala Lys Glu
                565                 570                 575

Asn Ile Asp Val Ser Val Val Ser Met Pro Ser Met Asp Arg Phe Glu
                580                 585                 590

Lys Gln Ser Asp Glu Tyr Lys Asn Glu Val Leu Pro Ala Asp Val Lys
            595                 600                 605

Lys Arg Leu Ala Ile Glu Met Gly Ser Ser Phe Gly Trp Gly Lys Tyr
        610                 615                 620

Thr Gly Leu Glu Gly Asp Val Leu Gly Ile Asp Arg Phe Gly Ala Ser
625                 630                 635                 640

Ala Pro Gly Glu Thr Ile Ile Asn Glu Tyr Gly Phe Ser Val Pro Asn
                645                 650                 655

Val Val Asn Arg Val Lys Ala Leu Ile Asn Lys
                660                 665

<210> SEQ ID NO 3
<211> LENGTH: 37
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggagaaatc atatggatac aattgaaaag aaatcag                               37

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggacatactg ccggtgttga tg                                               22

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aattaaatga attcattaaa gaggagaaat catatg                                36

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aattaaatgg atcccttatt gattaatgcc ttaac                                 35

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gttctgaggt cattactgg                                                   19

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggacatactg ccggtgttga tg                                               22

<210> SEQ ID NO 9
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 9
ttgaagaatt aacagcggc                                                    19

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagcttgaac tggcaatc                                                     18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtcctgcgat tcgccttg                                                     18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acgaaacacc cgacgctc                                                     18

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aattaaatgg atccttactt attgattaat gccttaac                               38

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggatgccaaa ctgcttcc                                                     18

<210> SEQ ID NO 15
<211> LENGTH: 37
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 15
agcagtttgg catccaacgc atcttccggt gaagttc                              37

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agcagtttgg catcccaagc atcttccggt gaagttc                              37

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agcagtttgg catccgcagc atcttccggt gaagttc                              37

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agcagtttgg catccaaagc atcttccggt gaagttc                              37

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agcagtttgg catcctcagc atcttccggt gaagttc                              37

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agcagtttgg catccacagc atcttccggt gaagttc                              37

<210> SEQ ID NO 21
<211> LENGTH: 37
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 21
agcagtttgg catcccatgc atcttccggt gaagttc                              37

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agcagtttgg catccgtggc atcttccggt gaagttc                              37

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agcagtttgg catccattgc atcttccggt gaagttc                              37

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agcagtttgg catccttggc atcttccggt gaagttc                              37

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agcagtttgg catccatggc atcttccggt gaagttc                              37

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agcagtttgg catccggtgc atcttccggt gaagttc                              37

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 27
ggggcagcaa aacaccagga c                                                    21

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gatctcgacc ctgcagccca agcacacagg aacctcttga tccc                           44

<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcgtcaaaac gcataccatt ttgaacaaaa ccttcctacc atcgatc                        47

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cttattgatt aatgccttaa ctcg                                                 24

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 31

His His His His His His
1               5

<210> SEQ ID NO 32
<211> LENGTH: 663
<212> TYPE: PRT
<213> ORGANISM: Escherichia coli

<400> SEQUENCE: 32

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
                20                  25                  30

Met Ala Asp Ile Ala Glu Val Leu Trp Arg Asp Phe Leu Lys His Asn
            35                  40                  45

Pro Gln Asn Pro Ser Trp Ala Asp Arg Asp Arg Phe Val Leu Ser Asn
        50                  55                  60

```
Gly His Gly Ser Met Leu Ile Tyr Ser Leu Leu His Leu Thr Gly Tyr
 65                  70                  75                  80

Asp Leu Pro Met Glu Glu Leu Lys Asn Phe Arg Gln Leu His Ser Lys
                 85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
                180                 185                 190

Val Glu Gly Trp Phe Thr Asp Asp Thr Ala Met Arg Phe Glu Ala Tyr
            195                 200                 205

Gly Trp His Val Ile Arg Asp Ile Asp Gly His Asp Ala Ala Ser Ile
        210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Gln Ala Lys Glu
    290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
        355                 360                 365

Gly Pro Leu Leu Pro Glu Phe Leu Gly Gly Ser Ala Asp Leu Ala Pro
    370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
        435                 440                 445

Ala Leu Met Lys Gln Arg Gln Val Met Val Tyr Thr His Asp Ser Ile
    450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
```

```
            485                 490                 495
Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
            515                 520                 525

Thr Glu Glu Gln Leu Ala Asn Ile Ala Arg Gly Gly Tyr Val Leu Lys
            530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575

Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
            595                 600                 605

Val Ala Val Glu Ala Gly Ile Ala Asp Tyr Trp Tyr Lys Tyr Val Gly
            610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
                645                 650                 655

Ala Lys Ala Lys Glu Leu Leu
            660

<210> SEQ ID NO 33
<211> LENGTH: 667
<212> TYPE: PRT
<213> ORGANISM: Escherichia coli

<400> SEQUENCE: 33

Met Ser Arg Lys Asp Leu Ala Asn Ala Ile Arg Ala Leu Ser Met Asp
1               5                   10                  15

Ala Val Gln Lys Ala Asn Ser Gly His Pro Gly Ala Pro Met Gly Met
                20                  25                  30

Ala Asp Ile Ala Glu Val Leu Trp Asn Asp Phe Leu Lys His Asn Pro
            35                  40                  45

Thr Asp Pro Thr Trp Tyr Asp Arg Asp Arg Phe Ile Leu Ser Asn Gly
        50                  55                  60

His Ala Ser Met Leu Leu Tyr Ser Leu Leu His Leu Thr Gly Tyr Asp
65                  70                  75                  80

Leu Pro Leu Glu Glu Leu Lys Asn Phe Arg Gln Leu His Ser Lys Thr
                85                  90                  95

Pro Gly His Pro Glu Ile Gly Tyr Thr Pro Gly Val Glu Thr Thr Thr
            100                 105                 110

Gly Pro Leu Gly Gln Gly Leu Ala Asn Ala Val Gly Leu Ala Ile Ala
            115                 120                 125

Glu Arg Thr Leu Ala Ala Gln Phe Asn Gln Pro Asp His Glu Ile Val
            130                 135                 140

Asp His Phe Thr Tyr Val Phe Met Gly Asp Gly Cys Leu Met Glu Gly
145                 150                 155                 160

Ile Ser His Glu Val Cys Ser Leu Ala Gly Thr Leu Gly Leu Gly Lys
                165                 170                 175

Leu Ile Gly Phe Tyr Asp His Asn Gly Ile Ser Ile Asp Gly Glu Thr
            180                 185                 190
```

-continued

```
Glu Gly Trp Phe Thr Asp Asp Thr Ala Lys Arg Phe Glu Ala Tyr His
            195                 200                 205

Trp His Val Ile His Glu Ile Asp Gly His Asp Pro Gln Ala Val Lys
210                 215                 220

Glu Ala Ile Leu Glu Ala Gln Ser Val Lys Asp Lys Pro Ser Leu Ile
225                 230                 235                 240

Ile Cys Arg Thr Val Ile Gly Phe Gly Ser Pro Asn Lys Ala Gly Lys
            245                 250                 255

Glu Glu Ala His Gly Ala Pro Leu Glu Glu Glu Val Ala Leu Ala
            260                 265                 270

Arg Gln Lys Leu Gly Trp His His Pro Pro Phe Glu Ile Pro Lys Glu
            275                 280                 285

Ile Tyr His Ala Trp Asp Ala Arg Glu Lys Gly Glu Lys Ala Gln Gln
    290                 295                 300

Ser Trp Asn Glu Lys Phe Ala Ala Tyr Lys Lys Ala His Pro Gln Leu
305                 310                 315                 320

Ala Glu Glu Phe Thr Arg Arg Met Ser Gly Gly Leu Pro Lys Asp Trp
                325                 330                 335

Glu Lys Thr Thr Gln Lys Tyr Ile Asn Glu Leu Gln Ala Asn Pro Ala
            340                 345                 350

Lys Ile Ala Thr Arg Lys Ala Ser Gln Asn Thr Leu Asn Ala Tyr Gly
            355                 360                 365

Pro Met Leu Pro Glu Leu Leu Gly Gly Ser Ala Asp Leu Ala Pro Ser
    370                 375                 380

Asn Leu Thr Ile Trp Lys Gly Ser Val Ser Leu Lys Glu Asp Pro Ala
385                 390                 395                 400

Gly Asn Tyr Ile His Tyr Gly Val Arg Glu Phe Gly Met Thr Ala Ile
                405                 410                 415

Ala Asn Gly Ile Ala His His Gly Gly Phe Val Pro Tyr Thr Ala Thr
            420                 425                 430

Phe Leu Met Phe Val Glu Tyr Ala Arg Asn Ala Ala Arg Met Ala Ala
    435                 440                 445

Leu Met Lys Ala Arg Gln Ile Met Val Tyr Thr His Asp Ser Ile Gly
450                 455                 460

Leu Gly Glu Asp Gly Pro Thr His Gln Ala Val Glu Gln Leu Ala Ser
465                 470                 475                 480

Leu Arg Leu Thr Pro Asn Phe Ser Thr Trp Arg Pro Cys Asp Gln Val
                485                 490                 495

Glu Ala Ala Val Gly Trp Lys Leu Ala Val Glu Arg His Asn Gly Pro
            500                 505                 510

Thr Ala Leu Ile Leu Ser Arg Gln Asn Leu Ala Gln Val Glu Arg Thr
            515                 520                 525

Pro Asp Gln Val Lys Glu Ile Ala Arg Gly Gly Tyr Val Leu Lys Asp
    530                 535                 540

Ser Gly Gly Lys Pro Asp Ile Ile Leu Ile Ala Thr Gly Ser Glu Met
545                 550                 555                 560

Glu Ile Thr Leu Gln Ala Ala Glu Lys Leu Ala Gly Glu Gly Arg Asn
                565                 570                 575

Val Arg Val Val Ser Leu Pro Ser Thr Asp Ile Phe Asp Ala Gln Asp
            580                 585                 590

Glu Glu Tyr Arg Glu Ser Val Leu Pro Ser Asn Val Ala Ala Arg Val
    595                 600                 605

Ala Val Glu Ala Gly Ile Ala Asp Tyr Trp Tyr Lys Tyr Val Gly Leu
```

```
                   610                 615                 620
Lys Gly Ala Ile Val Gly Met Thr Gly Tyr Gly Glu Ser Ala Pro Ala
625                 630                 635                 640

Asp Lys Leu Phe Pro Phe Phe Gly Phe Thr Ala Glu Asn Ile Val Ala
                    645                 650                 655

Lys Ala His Lys Val Leu Gly Val Lys Gly Ala
                660                 665

<210> SEQ ID NO 34
<211> LENGTH: 667
<212> TYPE: PRT
<213> ORGANISM: Bacillus subtilis

<400> SEQUENCE: 34

Met Asp Thr Ile Glu Lys Lys Ser Val Ala Thr Ile Arg Thr Leu Ser
1               5                   10                  15

Ile Asp Ala Ile Glu Lys Ala Asn Ser Gly His Pro Gly Met Pro Met
                20                  25                  30

Gly Ala Ala Pro Met Ala Tyr Thr Leu Trp Thr Lys Phe Met Asn Val
            35                  40                  45

Ser Pro Ala Asn Pro Gly Trp Phe Asn Arg Asp Arg Phe Val Leu Ser
50                  55                  60

Ala Gly His Gly Ser Ala Leu Leu Tyr Ser Met Leu His Leu Ser Gly
65                  70                  75                  80

Phe Asp Leu Ser Ile Glu Asp Leu Lys Gly Phe Arg Gln Trp Gly Ser
                85                  90                  95

Lys Thr Pro Gly His Pro Glu Phe Gly His Thr Ala Gly Val Asp Ala
            100                 105                 110

Thr Thr Gly Pro Leu Gly Gln Gly Ile Ala Met Ala Val Gly Met Ala
        115                 120                 125

Ile Ala Glu Arg His Leu Ala Glu Thr Tyr Asn Arg Asp Ser Phe Asn
130                 135                 140

Val Val Asp His Tyr Thr Tyr Ser Ile Cys Gly Asp Gly Asp Leu Met
145                 150                 155                 160

Glu Gly Ile Ser Ser Glu Ala Ala Ser Leu Ala Gly His Leu Gln Leu
                165                 170                 175

Gly Arg Leu Ile Val Leu Tyr Asp Ser Asn Asp Ile Ser Leu Asp Gly
            180                 185                 190

Asp Leu Asp Arg Ser Phe Ser Glu Asn Val Lys Gln Arg Phe Glu Ala
        195                 200                 205

Met Asn Trp Glu Val Leu Tyr Val Glu Asp Gly Asn Asn Ile Glu Glu
210                 215                 220

Leu Thr Ala Ala Ile Glu Lys Ala Arg Gln Asn Glu Lys Lys Pro Thr
225                 230                 235                 240

Leu Ile Glu Val Lys Thr Thr Ile Gly Phe Gly Ser Pro Asn Arg Ala
                245                 250                 255

Gly Thr Ser Gly Val His Gly Ala Pro Leu Gly Lys Glu Glu Ser Lys
            260                 265                 270

Leu Thr Lys Glu Ala Tyr Ala Trp Thr Tyr Glu Glu Asp Phe Tyr Val
        275                 280                 285

Pro Ser Glu Val Tyr Glu His Phe Ala Val Ala Val Lys Glu Ser Gly
        290                 295                 300

Glu Lys Lys Glu Gln Glu Trp Asn Ala Gln Phe Ala Lys Tyr Lys Glu
305                 310                 315                 320
```

```
Val Tyr Pro Glu Leu Ala Glu Gln Leu Glu Leu Ala Ile Lys Gly Glu
            325                 330                 335

Leu Pro Lys Asp Trp Asp Gln Glu Val Pro Val Tyr Lys Gly Ser
        340                 345                 350

Ser Leu Ala Ser Arg Ala Ser Ser Gly Glu Val Leu Asn Gly Leu Ala
        355                 360                 365

Lys Lys Ile Pro Phe Phe Val Gly Ser Ala Asp Leu Ala Gly Ser
370                 375                 380

Asn Lys Thr Thr Ile Lys Asn Ala Gly Asp Phe Thr Ala Val Asp Tyr
385                 390                 395                 400

Ser Gly Lys Asn Phe Trp Phe Gly Val Arg Glu Phe Ala Met Gly Ala
                405                 410                 415

Ala Leu Asn Gly Met Ala Leu His Gly Gly Leu Arg Val Phe Gly Gly
                420                 425                 430

Thr Phe Phe Val Phe Ser Asp Tyr Leu Arg Pro Ala Ile Arg Leu Ala
                435                 440                 445

Ala Leu Met Gly Leu Pro Val Thr Tyr Val Phe Thr His Asp Ser Ile
            450                 455                 460

Ala Val Gly Glu Asp Gly Pro Thr His Glu Pro Val Glu Gln Leu Ala
465                 470                 475                 480

Ser Leu Arg Ala Met Pro Asn Leu Ser Leu Ile Arg Pro Ala Asp Gly
                485                 490                 495

Asn Glu Thr Ala Ala Ala Trp Lys Leu Ala Val Gln Ser Thr Asp His
                500                 505                 510

Pro Thr Ala Leu Val Leu Thr Arg Gln Asn Leu Pro Thr Ile Asp Gln
            515                 520                 525

Thr Ser Glu Glu Ala Leu Ala Gly Val Glu Lys Gly Ala Tyr Val Val
530                 535                 540

Ser Lys Ser Lys Asn Glu Thr Pro Asp Ala Leu Leu Ile Ala Ser Gly
545                 550                 555                 560

Ser Glu Val Gly Leu Ala Ile Glu Ala Gln Ala Glu Leu Ala Lys Glu
                565                 570                 575

Asn Ile Asp Val Ser Val Val Ser Met Pro Ser Met Asp Arg Phe Glu
                580                 585                 590

Lys Gln Ser Asp Glu Tyr Lys Asn Glu Val Leu Pro Ala Asp Val Lys
            595                 600                 605

Lys Arg Leu Ala Ile Glu Met Gly Ser Ser Phe Gly Trp Gly Lys Tyr
            610                 615                 620

Thr Gly Leu Glu Gly Asp Val Leu Gly Ile Asp Arg Phe Gly Ala Ser
625                 630                 635                 640

Ala Pro Gly Glu Thr Ile Ile Asn Glu Tyr Gly Phe Ser Val Pro Asn
                645                 650                 655

Val Val Asn Arg Val Lys Ala Leu Ile Asn Lys
                660                 665

<210> SEQ ID NO 35
<211> LENGTH: 667
<212> TYPE: PRT
<213> ORGANISM: Bacillus licheniformis

<400> SEQUENCE: 35

Met Lys Thr Ile Glu Leu Lys Ser Val Ala Thr Ile Arg Thr Leu Ser
1               5                   10                  15

Ile Asp Ala Ile Glu Lys Ala Lys Ser Gly His Pro Gly Met Pro Met
            20                  25                  30
```

```
Gly Thr Ala Pro Met Ala Tyr Ala Leu Trp Thr Lys Met Met Asn Val
            35                  40                  45

Ser Pro Glu Asn Pro Asn Trp Phe Asn Arg Asp Arg Phe Val Leu Ser
 50                  55                  60

Ala Gly His Gly Ser Met Leu Leu Tyr Ser Met Leu His Leu Ser Gly
 65                  70                  75                  80

Tyr Asp Val Ser Ile Glu Asp Leu Lys Asn Phe Arg Gln Trp Gly Ser
                85                  90                  95

Lys Thr Pro Gly His Pro Glu Phe Gly His Thr Pro Gly Val Asp Ala
            100                 105                 110

Thr Thr Gly Pro Leu Gly Gln Gly Ile Gly Met Ala Val Gly Met Ala
            115                 120                 125

Leu Ala Glu Arg His Leu Ala Glu Thr Tyr Asn Arg Asp Asp Tyr Arg
            130                 135                 140

Val Val Asp His Tyr Thr Tyr Ser Ile Cys Gly Asp Gly Asp Leu Met
145                 150                 155                 160

Glu Gly Ile Ser Ser Glu Ala Ala Ser Leu Ala Gly His Leu Asn Leu
                165                 170                 175

Gly Arg Leu Ile Val Leu Tyr Asp Ser Asn Asp Ile Ser Leu Asp Gly
            180                 185                 190

Glu Leu Asn Arg Ser Phe Ser Glu Asn Val Lys Gln Arg Phe Glu Ala
            195                 200                 205

Met Asn Trp Glu Val Leu Tyr Val Glu Asp Gly Asn Asn Ile Ala Glu
210                 215                 220

Ile Thr Ala Ala Ile Glu Lys Ala Lys Gln Asn Glu Lys Gln Pro Thr
225                 230                 235                 240

Leu Ile Glu Val Lys Thr Thr Ile Gly Phe Gly Ser Pro Asn Arg Ala
                245                 250                 255

Gly Thr Ser Gly Val His Gly Ala Pro Leu Gly Ser Glu Glu Ala Lys
            260                 265                 270

Leu Thr Lys Glu Ala Tyr Glu Trp Thr Tyr Glu Glu Asp Phe Tyr Val
            275                 280                 285

Pro Ser Glu Val Tyr Glu His Phe Asn Glu Thr Val Lys Glu Ala Gly
            290                 295                 300

Lys Lys Lys Glu Ala Glu Trp Asn Glu Leu Phe Ser Ala Tyr Lys Lys
305                 310                 315                 320

Ala His Pro Glu Leu Ala Glu Glu Leu Glu Leu Ala Ile Lys Gly Glu
                325                 330                 335

Leu Pro Glu Gly Trp Asp Gln Lys Val Pro Val Tyr Glu Lys Gly Ser
            340                 345                 350

Ser Leu Ala Ser Arg Ala Ser Ser Gly Glu Val Leu Asn Gly Ile Ala
            355                 360                 365

Gln Gln Val Pro Phe Phe Phe Gly Gly Ser Ala Asp Leu Ala Gly Ser
            370                 375                 380

Asn Lys Thr Thr Ile Lys Asn Gly Gly Asp Val Ser Ala Lys Asp Tyr
385                 390                 395                 400

Ala Gly Arg Asn Ile Trp Phe Gly Val Arg Glu Phe Ala Met Gly Ala
                405                 410                 415

Ala Leu Asn Gly Met Ala Leu His Gly Gly Leu Arg Val Phe Gly Gly
            420                 425                 430

Thr Phe Phe Val Phe Ser Asp Tyr Leu Arg Pro Ala Ile Arg Leu Ala
            435                 440                 445
```

```
Ala Leu Met Gly Leu Pro Val Thr Tyr Val Phe Thr His Asp Ser Ile
    450                 455                 460
Ala Val Gly Glu Asp Gly Pro Thr His Glu Pro Ile Glu Gln Leu Ala
465                 470                 475                 480
Ser Leu Arg Ala Leu Pro Asn Leu Ser Val Ile Arg Pro Ala Asp Gly
                485                 490                 495
Asn Glu Thr Ala Ala Ala Trp Lys Leu Ala Leu Gln Ser Lys Asp Gln
            500                 505                 510
Pro Thr Ala Leu Val Leu Thr Arg Gln Asn Leu Pro Thr Ile Asp Gln
        515                 520                 525
Ser Ala Glu Thr Ala Tyr Glu Gly Val Lys Lys Gly Ala Tyr Val Val
530                 535                 540
Ser Lys Ser Gln Asn Glu Lys Pro Glu Ala Ile Leu Leu Ala Ser Gly
545                 550                 555                 560
Ser Glu Val Gly Leu Ala Leu Asp Ala Gln Ser Glu Leu Gln Lys Glu
                565                 570                 575
Gly Ile Asp Val Ser Val Val Ser Val Pro Ser Trp Asp Arg Phe Asp
            580                 585                 590
Lys Gln Pro Ala Glu Tyr Lys Asn Ala Val Leu Pro Thr Asp Val Thr
        595                 600                 605
Lys Arg Leu Ala Ile Glu Met Gly Ser Pro Leu Gly Trp Glu Arg Tyr
610                 615                 620
Thr Gly Thr Asp Gly Asp Ile Leu Gly Ile Asp Gln Phe Gly Ala Ser
625                 630                 635                 640
Ala Pro Gly Glu Thr Ile Met Lys Glu Tyr Gly Phe Thr Pro Ala Asn
                645                 650                 655
Val Val Asp Arg Val Lys Lys Leu Leu Asn Arg
            660                 665

<210> SEQ ID NO 36
<211> LENGTH: 666
<212> TYPE: PRT
<213> ORGANISM: Bacillus halodurans

<400> SEQUENCE: 36

Met Ser Lys His Val Glu Gln Leu Ala Val Asn Thr Ile Arg Thr Leu
1               5                   10                  15
Ser Ile Asp Ser Val Glu Lys Ala Asn Ser Gly His Pro Gly Met Pro
            20                  25                  30
Met Gly Ala Ala Pro Met Ala Phe Cys Leu Trp Thr Lys Phe Met Asn
        35                  40                  45
His Asn Pro Ala Asn Pro Asp Trp Val Asn Arg Asp Arg Phe Val Leu
    50                  55                  60
Ser Ala Gly His Gly Ser Met Leu Leu Tyr Ser Leu Leu His Leu Thr
65                  70                  75                  80
Gly Tyr Asp Leu Ser Leu Glu Glu Leu Gln Asn Phe Arg Gln Trp Gly
                85                  90                  95
Ser Lys Thr Pro Gly His Pro Glu Tyr Gly His Thr Pro Gly Val Glu
            100                 105                 110
Ala Thr Thr Gly Pro Leu Gly Gln Gly Val Ala Met Ala Val Gly Met
        115                 120                 125
Ala Met Ala Glu Arg His Leu Ala Ala Thr Tyr Asn Arg Asp Gly Tyr
    130                 135                 140
Asn Ile Val Asp His Tyr Thr Tyr Thr Ile Cys Gly Asp Gly Asp Leu
145                 150                 155                 160
```

```
Met Glu Gly Val Ser Ala Glu Ala Ser Leu Ala Gly His Leu Lys
                165                 170                 175

Leu Gly Arg Met Ile Leu Leu Tyr Asp Ser Asn Asp Ile Ser Leu Asp
            180                 185                 190

Gly Asp Leu His His Ser Phe Ser Glu Ser Val Glu Asp Arg Phe Lys
                195                 200                 205

Ala Tyr Gly Trp His Val Val Arg Val Glu Asp Gly Asn Asn Leu Asp
        210                 215                 220

Glu Ile Ala Lys Ala Ile Glu Glu Ala Lys Ala Asp Glu Arg Pro Ser
225                 230                 235                 240

Leu Ile Glu Val Lys Thr Thr Ile Gly Phe Gly Ser Pro Asn Lys Gly
                245                 250                 255

Gly Lys Ser Val Ser His Gly Ala Pro Leu Gly Ala Asp Glu Val Lys
            260                 265                 270

Leu Thr Lys Glu Ala Tyr Glu Trp Thr Tyr Glu Asn Glu Phe His Ile
        275                 280                 285

Pro Glu Glu Val Ala Ala Tyr Tyr Glu Gln Val Lys Gln Gln Gly Ala
    290                 295                 300

Glu Lys Glu Glu Ser Trp Asn Glu Leu Phe Ala Gln Tyr Lys Lys Ala
305                 310                 315                 320

Tyr Pro Glu Leu Ala Ser Gln Phe Glu Leu Ala Val His Gly Asp Leu
                325                 330                 335

Pro Glu Gly Trp Asp Ala Val Ala Pro Ser Tyr Glu Val Gly Lys Ser
            340                 345                 350

Val Ala Thr Arg Ser Ser Gly Glu Ala Leu Asn Ala Phe Ala Lys
        355                 360                 365

Thr Val Pro Gln Leu Phe Gly Gly Ser Ala Asp Leu Ala Ser Ser Asn
        370                 375                 380

Lys Thr Leu Ile Lys Gly Glu Ala Asn Phe Ser Arg Asp Asp Tyr Ser
385                 390                 395                 400

Gly Arg Asn Val Trp Phe Gly Val Arg Glu Phe Ala Met Gly Ala Ala
                405                 410                 415

Met Asn Gly Met Ala Leu His Gly Gly Leu Lys Val Phe Gly Ala Thr
            420                 425                 430

Phe Phe Val Phe Ser Asp Tyr Leu Arg Pro Ala Ile Arg Leu Ala Ala
        435                 440                 445

Leu Met Gln Leu Pro Val Ile Tyr Val Phe Thr His Asp Ser Ile Ala
    450                 455                 460

Val Gly Glu Asp Gly Pro Thr His Glu Pro Val Glu Gln Leu Ala Ser
465                 470                 475                 480

Leu Arg Ala Met Pro Gly Leu Ser Val Ile Arg Pro Ala Asp Gly Asn
                485                 490                 495

Glu Ser Val Ala Ala Trp Lys Leu Ala Leu Glu Ser Lys Asp Gln Pro
            500                 505                 510

Thr Ala Leu Val Leu Ser Arg Gln Asn Leu Pro Thr Leu Glu Gly Ala
        515                 520                 525

Val Asp Arg Ala Tyr Asp Gly Val Ser Lys Gly Ala Tyr Val Leu Ala
    530                 535                 540

Pro Ala Asn Gly Ser Ala Asp Leu Leu Leu Ala Ser Gly Ser Glu
545                 550                 555                 560

Val Ser Leu Ala Val Asn Ala Lys Glu Ala Leu Glu Lys Glu Gly Ile
                565                 570                 575
```

His Ala Ala Val Val Ser Met Pro Ser Trp Asp Arg Phe Glu Ala Gln
            580                 585                 590

Ser Ala Glu Tyr Lys Glu Val Leu Pro Ser Asp Val Thr Ala Arg
        595                 600                 605

Leu Ala Ile Glu Met Gly Ser Ser Leu Gly Trp Ala Lys Tyr Val Gly
        610                 615                 620

Asn Gln Gly Asp Val Val Ala Ile Asp Arg Phe Gly Ala Ser Ala Pro
625                 630                 635                 640

Gly Glu Arg Ile Met Glu Phe Gly Phe Thr Val Gln His Val Val
            645                 650                 655

Ala Arg Ala Lys Ala Leu Leu Glu Asn Lys
            660                 665

<210> SEQ ID NO 37
<211> LENGTH: 700
<212> TYPE: PRT
<213> ORGANISM: Corynebacterium glutamicum

<400> SEQUENCE: 37

Met Thr Thr Leu Thr Leu Ser Pro Glu Leu Gln Ala Leu Thr Val Arg
1               5                   10                  15

Asn Tyr Pro Ser Asp Trp Ser Asp Val Asp Thr Lys Ala Val Asp Thr
            20                  25                  30

Val Arg Val Leu Ala Ala Asp Ala Val Glu Asn Cys Gly Ser Gly His
        35                  40                  45

Pro Gly Thr Ala Met Ser Leu Ala Pro Leu Ala Tyr Thr Leu Tyr Gln
    50                  55                  60

Arg Val Met Asn Val Asp Pro Gln Asp Thr Asn Trp Ala Gly Arg Asp
65                  70                  75                  80

Arg Phe Val Leu Ser Cys Gly His Ser Ser Leu Thr Gln Tyr Ile Gln
                85                  90                  95

Leu Tyr Leu Gly Gly Phe Gly Leu Glu Met Asp Asp Leu Lys Ala Leu
            100                 105                 110

Arg Thr Trp Asp Ser Leu Thr Pro Gly His Pro Glu Tyr Arg His Thr
        115                 120                 125

Lys Gly Val Glu Ile Thr Thr Gly Pro Leu Gly Gln Gly Leu Ala Ser
    130                 135                 140

Ala Val Gly Met Ala Met Ala Ala Arg Arg Glu Arg Gly Leu Phe Asp
145                 150                 155                 160

Pro Thr Ala Ala Glu Gly Glu Ser Pro Phe Asp His His Ile Tyr Val
                165                 170                 175

Ile Ala Ser Asp Gly Asp Leu Gln Glu Gly Val Thr Ser Glu Ala Ser
            180                 185                 190

Ser Ile Ala Gly Thr Gln Gln Leu Gly Asn Leu Ile Val Phe Trp Asp
        195                 200                 205

Asp Asn Arg Ile Ser Ile Glu Asp Asn Thr Glu Ile Ala Phe Asn Glu
    210                 215                 220

Asp Val Val Ala Arg Tyr Lys Ala Tyr Gly Trp Gln Thr Ile Glu Val
225                 230                 235                 240

Glu Ala Gly Glu Asp Val Ala Ala Ile Glu Ala Val Ala Glu Ala
                245                 250                 255

Lys Lys Asp Thr Lys Arg Pro Thr Phe Ile Arg Val Arg Thr Ile Ile
            260                 265                 270

Gly Phe Pro Ala Pro Thr Met Met Asn Thr Gly Ala Val His Gly Ala
        275                 280                 285

```
Ala Leu Gly Ala Ala Glu Val Ala Thr Lys Thr Glu Leu Gly Phe
    290                 295                 300

Asp Pro Glu Ala His Phe Ala Ile Asp Asp Glu Val Ile Ala His Thr
305                 310                 315                 320

Arg Ser Leu Ala Glu Arg Ala Ala Gln Lys Lys Ala Ala Trp Gln Val
                325                 330                 335

Lys Phe Asp Glu Trp Ala Ala Ala Asn Pro Glu Asn Lys Ala Leu Phe
            340                 345                 350

Asp Arg Leu Asn Ser Arg Glu Leu Pro Ala Gly Tyr Ala Asp Glu Leu
        355                 360                 365

Pro Thr Trp Asp Ala Asp Glu Lys Gly Val Ala Thr Arg Lys Ala Ser
    370                 375                 380

Glu Ala Ala Leu Gln Ala Leu Gly Lys Thr Leu Pro Glu Leu Trp Gly
385                 390                 395                 400

Gly Ser Ala Asp Leu Ala Gly Ser Asn Asn Thr Val Ile Lys Gly Ser
                405                 410                 415

Pro Ser Phe Gly Pro Glu Ser Ile Ser Thr Glu Thr Trp Ser Ala Glu
            420                 425                 430

Pro Tyr Gly Arg Asn Leu His Phe Gly Ile Arg Glu His Ala Met Gly
        435                 440                 445

Ser Ile Leu Asn Gly Ile Ser Leu His Gly Gly Thr Arg Pro Tyr Gly
    450                 455                 460

Gly Thr Phe Leu Ile Phe Ser Asp Tyr Met Arg Pro Ala Val Arg Leu
465                 470                 475                 480

Ala Ala Leu Met Glu Thr Asp Ala Tyr Tyr Val Trp Thr His Asp Ser
                485                 490                 495

Ile Gly Leu Gly Glu Asp Gly Pro Thr His Gln Pro Val Glu Thr Leu
            500                 505                 510

Ala Ala Leu Arg Ala Ile Pro Gly Leu Ser Val Leu Arg Pro Ala Asp
        515                 520                 525

Ala Asn Glu Thr Ala Gln Ala Trp Ala Ala Ala Leu Glu Tyr Lys Glu
    530                 535                 540

Gly Pro Lys Gly Leu Ala Leu Thr Arg Gln Asn Val Pro Val Leu Glu
545                 550                 555                 560

Gly Thr Lys Glu Lys Ala Ala Glu Gly Val Arg Arg Gly Gly Tyr Val
                565                 570                 575

Leu Val Glu Gly Ser Lys Glu Thr Pro Asp Val Ile Leu Met Gly Ser
            580                 585                 590

Gly Ser Glu Val Gln Leu Ala Val Asn Ala Ala Lys Ala Leu Glu Ala
        595                 600                 605

Glu Gly Val Ala Ala Arg Val Val Ser Val Pro Cys Met Asp Trp Phe
    610                 615                 620

Gln Glu Gln Asp Ala Glu Tyr Ile Glu Ser Val Leu Pro Ala Ala Val
625                 630                 635                 640

Thr Ala Arg Val Ser Val Glu Ala Gly Ile Ala Met Pro Trp Tyr Arg
                645                 650                 655

Phe Leu Gly Thr Gln Gly Arg Ala Val Ser Leu Glu His Phe Gly Ala
            660                 665                 670

Ser Ala Asp Tyr Gln Thr Leu Phe Glu Lys Phe Gly Ile Thr Thr Asp
        675                 680                 685

Ala Val Val Ala Ala Ala Lys Asp Ser Ile Asn Gly
    690                 695                 700
```

<210> SEQ ID NO 38
<211> LENGTH: 679
<212> TYPE: PRT
<213> ORGANISM: Saccharomyces cerevisiae

<400> SEQUENCE: 38

```
Thr Gln Phe Thr Asp Ile Asp Lys Leu Ala Val Ser Thr Ile Arg Ile
  1               5                  10                  15

Leu Ala Val Asp Thr Val Ser Lys Ala Asn Ser Gly His Pro Gly Ala
             20                  25                  30

Pro Leu Gly Met Ala Pro Ala Ala His Val Leu Trp Ser Gln Met Arg
         35                  40                  45

Met Asn Pro Thr Asn Pro Asp Trp Ile Asn Arg Asp Arg Phe Val Leu
 50                  55                  60

Ser Asn Gly His Ala Val Ala Leu Leu Tyr Ser Met Leu His Leu Thr
 65                  70                  75                  80

Gly Tyr Asp Leu Ser Ile Glu Asp Leu Lys Gln Phe Arg Gln Leu Gly
                 85                  90                  95

Ser Arg Thr Pro Gly His Pro Glu Phe Glu Leu Pro Gly Val Glu Val
            100                 105                 110

Thr Thr Gly Pro Leu Gly Gln Gly Ile Ser Asn Ala Val Gly Met Ala
        115                 120                 125

Met Ala Gln Ala Asn Leu Ala Ala Thr Tyr Asn Lys Pro Gly Phe Thr
130                 135                 140

Leu Ser Asp Asn Tyr Thr Tyr Val Phe Leu Gly Asp Gly Cys Leu Gln
145                 150                 155                 160

Glu Gly Ile Ser Ser Glu Ala Ser Ser Leu Ala Gly His Leu Lys Leu
                165                 170                 175

Gly Asn Leu Ile Ala Ile Tyr Asp Asp Asn Lys Ile Thr Ile Asp Gly
            180                 185                 190

Ala Thr Ser Ile Ser Phe Asp Glu Asp Val Ala Lys Arg Tyr Glu Ala
        195                 200                 205

Tyr Gly Trp Glu Val Leu Tyr Val Glu Asn Gly Asn Glu Asp Leu Ala
210                 215                 220

Gly Ile Ala Lys Ala Ile Ala Gln Ala Lys Leu Ser Lys Asp Lys Pro
225                 230                 235                 240

Thr Leu Ile Lys Met Thr Thr Thr Ile Gly Tyr Gly Ser Leu His Ala
                245                 250                 255

Gly Ser His Ser Val His Gly Ala Pro Leu Lys Ala Asp Asp Val Lys
            260                 265                 270

Gln Leu Lys Ser Lys Phe Gly Phe Asn Pro Asp Lys Ser Phe Val Val
        275                 280                 285

Pro Gln Glu Val Tyr Asp His Tyr Gln Lys Thr Ile Leu Lys Pro Gly
290                 295                 300

Val Glu Ala Asn Asn Lys Trp Asn Lys Leu Phe Ser Glu Tyr Gln Lys
305                 310                 315                 320

Lys Phe Pro Glu Leu Gly Ala Glu Leu Ala Arg Arg Leu Ser Gly Gln
                325                 330                 335

Leu Pro Ala Asn Trp Glu Ser Lys Leu Pro Thr Tyr Thr Ala Lys Asp
            340                 345                 350

Ser Ala Val Ala Thr Arg Lys Leu Ser Glu Thr Val Leu Glu Asp Val
        355                 360                 365

Tyr Asn Gln Leu Pro Glu Leu Ile Gly Gly Ser Ala Asp Leu Thr Pro
370                 375                 380
```

Ser Asn Leu Thr Arg Trp Lys Glu Ala Leu Asp Phe Gln Pro Pro Ser
385                 390                 395                 400

Ser Gly Ser Gly Asn Tyr Ser Gly Arg Tyr Ile Arg Tyr Gly Ile Arg
            405                 410                 415

Glu His Ala Met Gly Ala Ile Met Asn Gly Ile Ser Ala Phe Gly Ala
            420                 425                 430

Asn Tyr Lys Pro Tyr Gly Gly Thr Phe Leu Asn Phe Val Ser Tyr Ala
        435                 440                 445

Ala Gly Ala Val Arg Leu Ser Ala Leu Ser Gly His Pro Val Ile Trp
    450                 455                 460

Val Ala Thr His Asp Ser Ile Gly Val Gly Glu Asp Gly Pro Thr His
465                 470                 475                 480

Gln Pro Ile Glu Thr Leu Ala His Phe Arg Ser Leu Pro Asn Ile Gln
                485                 490                 495

Val Trp Arg Pro Ala Asp Gly Asn Glu Val Ser Ala Ala Tyr Lys Asn
            500                 505                 510

Ser Leu Glu Ser Lys His Thr Pro Ser Ile Ile Ala Leu Ser Arg Gln
        515                 520                 525

Asn Leu Pro Gln Leu Glu Gly Ser Ser Ile Glu Ser Ala Ser Lys Gly
    530                 535                 540

Gly Tyr Val Leu Gln Asp Val Ala Asn Pro Asp Ile Ile Leu Val Ala
545                 550                 555                 560

Thr Gly Ser Glu Val Ser Leu Ser Val Glu Ala Ala Lys Thr Leu Ala
                565                 570                 575

Ala Lys Asn Ile Lys Ala Arg Val Val Ser Leu Pro Asp Phe Phe Thr
            580                 585                 590

Phe Asp Lys Gln Pro Leu Glu Tyr Arg Leu Ser Val Leu Pro Asp Asn
        595                 600                 605

Val Pro Ile Met Ser Val Glu Val Leu Ala Thr Thr Cys Trp Gly Lys
    610                 615                 620

Tyr Ala His Gln Ser Phe Gly Ile Asp Arg Phe Gly Ala Ser Gly Lys
625                 630                 635                 640

Ala Pro Glu Val Phe Lys Phe Gly Phe Thr Pro Glu Gly Val Ala
                645                 650                 655

Glu Arg Ala Gln Lys Thr Ile Ala Phe Tyr Lys Gly Asp Lys Leu Ile
            660                 665                 670

Ser Pro Leu Lys Lys Ala Phe
        675

<210> SEQ ID NO 39
<211> LENGTH: 680
<212> TYPE: PRT
<213> ORGANISM: Ashbya gossypii

<400> SEQUENCE: 39

Met Thr Gln Phe Ser Asp Val Asp Arg Leu Ala Val Ser Thr Ile Arg
1               5                   10                  15

Leu Leu Ser Val Asp Gln Val Ser Lys Ala Asn Ser Gly His Pro Gly
            20                  25                  30

Ala Pro Leu Gly Leu Ala Pro Ala His Val Val Trp Lys Gln Met
        35                  40                  45

Arg Leu Asn Pro Lys Ser Pro Lys Trp Ile Asn Arg Asp Arg Phe Val
    50                  55                  60

Leu Ser Asn Gly His Ala Cys Ala Leu Leu Tyr Ser Leu Leu His Leu

-continued

```
            65                  70                  75                  80
Phe Gly Tyr Asp Leu Ser Ile Glu Asp Leu Lys Gln Phe Arg Gln Val
                    85                  90                  95
Gly Ser Lys Thr Pro Gly His Pro Glu Tyr Glu Leu Pro Gly Val Glu
                100                 105                 110
Val Thr Thr Gly Pro Leu Gly Gln Gly Ile Ser Asn Ala Val Gly Leu
                115                 120                 125
Ala Ile Ala Gln Ala Asn Leu Ala Ala Thr Tyr Asn Lys Pro Gly Tyr
            130                 135                 140
Glu Leu Ser Asp Asn Tyr Thr Tyr Val Phe Leu Gly Asp Gly Cys Leu
145                 150                 155                 160
Gln Glu Gly Val Ser Ser Glu Ala Ser Ser Leu Ala Gly His Leu Lys
                165                 170                 175
Leu Gly Asn Leu Ile Ala Phe Tyr Asp Asp Asn Lys Ile Thr Ile Asp
                180                 185                 190
Gly His Thr Glu Val Ser Phe Asp Glu Asp Val Leu Lys Arg Tyr Glu
            195                 200                 205
Ala Tyr Gly Trp Glu Val Leu Asn Val Ala Asn Gly Asp Glu Asn Leu
            210                 215                 220
Glu Asp Ile Ala Ser Ala Leu Glu Gln Ala Lys Lys Asn Lys Asp Lys
225                 230                 235                 240
Pro Thr Leu Ile Lys Leu Thr Thr Thr Ile Gly Phe Gly Ser Leu Asn
                245                 250                 255
Ala Gly Ser His Thr Val His Gly Ala Pro Leu Lys Ala Asp Asp Val
                260                 265                 270
Lys Gln Leu Lys Thr Lys Leu Gly Phe Asn Pro Asp Glu Ser Phe Ile
            275                 280                 285
Val Pro Gln Glu Val Tyr Asp Leu Tyr His Asn Ser Thr Ile Gln Pro
            290                 295                 300
Gly Ala Glu Ser Glu Lys Glu Trp Asn Ala Leu Leu Glu Lys Tyr Ala
305                 310                 315                 320
Gly Glu Tyr Pro Lys Glu Ala Ala Glu Leu Lys Arg Arg Leu Ala Gly
                325                 330                 335
Lys Leu Pro Glu Asn Trp Glu Ser Lys Leu Pro Val Tyr Lys Pro Thr
                340                 345                 350
Asp Ser Ala Val Ala Ser Arg Lys Leu Ser Glu Ile Val Leu Gln Ser
            355                 360                 365
Ile Phe Glu Asp Val Pro Glu Leu Ile Gly Gly Ser Ala Asp Leu Thr
            370                 375                 380
Pro Ser Asn Leu Thr Arg Thr Thr Asn Ala Val Asp Phe Gln Pro Pro
385                 390                 395                 400
Gln Ser Gly Leu Gly Asp Tyr Ser Gly Arg Tyr Ile Arg Phe Gly Val
                405                 410                 415
Arg Glu His Gly Met Gly Ala Ile Ile Asn Gly Leu Ser Ala Tyr Gly
                420                 425                 430
Ala Asn Tyr Lys Val Phe Gly Ala Thr Phe Leu Asn Phe Val Ser Tyr
            435                 440                 445
Ala Ala Gly Ala Val Arg Leu Ala Ala Leu Ser Gly His Pro Val Ile
            450                 455                 460
Trp Ile Ala Thr His Asp Ser Ile Gly Leu Gly Glu Asp Gly Pro Thr
465                 470                 475                 480
His Gln Pro Ile Glu Thr Leu Ala His Leu Arg Ala Ile Pro Asn Met
                485                 490                 495
```

```
Met Val Trp Arg Pro Ala Asp Gly Asn Glu Val Ser Ala Ala Tyr Lys
            500                 505                 510

Val Ala Leu Glu Ser Gln Asp Thr Pro Ser Val Ile Ala Leu Ser Arg
        515                 520                 525

Gln Asn Leu Pro Gln Leu Asp Gly Ser Ser Ile Glu Lys Ala Ser Lys
    530                 535                 540

Gly Gly Tyr Ile Leu Gln Asp Val Glu Asn Pro Asp Ile Ala Ile Val
545                 550                 555                 560

Ser Thr Gly Ser Glu Val Gly Ile Ala Val Glu Ala Ala Lys Leu Leu
                565                 570                 575

Ala Glu Lys Asn Met Lys Val Arg Ile Val Ser Leu Pro Asp Phe His
            580                 585                 590

Thr Phe Ser Arg Gln Pro Lys Glu Tyr Gln Leu Ser Val Leu Pro Asp
        595                 600                 605

Arg Val Pro Ile Leu Ser Val Glu Val Leu Ser Thr Ser Gly Trp Ser
    610                 615                 620

Glu Tyr Ala His Gln Ser Phe Gly Leu Asn Arg Phe Gly Ala Ser Gly
625                 630                 635                 640

Lys Gly Pro Glu Val Tyr Lys Phe Phe Glu Phe Thr Pro Glu Gly Ile
                645                 650                 655

Ala Ser Arg Ala Glu Lys Thr Val Ala Phe Tyr Lys Gly Lys Glu Val
            660                 665                 670

Leu Ser Pro Leu Asn Lys Ala Phe
        675                 680

<210> SEQ ID NO 40
<211> LENGTH: 681
<212> TYPE: PRT
<213> ORGANISM: Saccharomyces cerevisiae

<400> SEQUENCE: 40

Met Ala Gln Phe Ser Asp Ile Asp Lys Leu Ala Val Ser Thr Leu Arg
1               5                   10                  15

Leu Leu Ser Val Asp Gln Val Glu Ser Ala Gln Ser Gly His Pro Gly
            20                  25                  30

Ala Pro Leu Gly Leu Ala Pro Val Ala His Val Ile Phe Lys Gln Leu
        35                  40                  45

Arg Cys Asn Pro Asn Asn Glu His Trp Ile Asn Arg Asp Arg Phe Val
    50                  55                  60

Leu Ser Asn Gly His Ser Cys Ala Leu Leu Tyr Ser Met Leu His Leu
65                  70                  75                  80

Leu Gly Tyr Asp Tyr Ser Ile Glu Asp Leu Arg Gln Phe Arg Gln Val
                85                  90                  95

Asn Ser Arg Thr Pro Gly His Pro Glu Phe His Ser Ala Gly Val Glu
            100                 105                 110

Ile Thr Ser Gly Pro Leu Gly Gln Gly Ile Ser Asn Ala Val Gly Met
        115                 120                 125

Ala Ile Ala Gln Ala Asn Phe Ala Ala Thr Tyr Asn Glu Asp Gly Phe
    130                 135                 140

Pro Ile Ser Asp Ser Tyr Thr Phe Ala Ile Val Gly Asp Gly Cys Leu
145                 150                 155                 160

Gln Glu Gly Val Ser Ser Glu Thr Ser Ser Leu Ala Gly His Leu Gln
                165                 170                 175

Leu Gly Asn Leu Ile Thr Phe Tyr Asp Ser Asn Ser Ile Ser Ile Asp
```

```
            180                 185                 190
Gly Lys Thr Ser Tyr Ser Phe Asp Glu Asp Val Leu Lys Arg Tyr Glu
            195                 200                 205
Ala Tyr Gly Trp Glu Val Met Glu Val Asp Lys Gly Asp Asp Asp Met
210                 215                 220
Glu Ser Ile Ser Ser Ala Leu Glu Lys Ala Lys Leu Ser Lys Asp Lys
225                 230                 235                 240
Pro Thr Ile Ile Lys Val Thr Thr Ile Gly Phe Gly Ser Leu Gln
                    245                 250                 255
Gln Gly Thr Ala Gly Val His Gly Ser Ala Leu Lys Ala Asp Asp Val
            260                 265                 270
Lys Gln Leu Lys Lys Arg Trp Gly Phe Asp Pro Asn Lys Ser Phe Val
            275                 280                 285
Val Pro Gln Glu Val Tyr Asp Tyr Tyr Lys Lys Thr Val Val Glu Pro
            290                 295                 300
Gly Gln Lys Leu Asn Glu Glu Trp Asp Arg Met Phe Glu Glu Tyr Lys
305                 310                 315                 320
Thr Lys Phe Pro Glu Lys Gly Lys Glu Leu Gln Arg Arg Leu Asn Gly
                    325                 330                 335
Glu Leu Pro Glu Gly Trp Lys His Leu Pro Lys Phe Thr Pro Asp
                    340                 345                 350
Asp Asp Ala Leu Ala Thr Arg Lys Thr Ser Gln Val Leu Thr Asn
            355                 360                 365
Met Val Gln Val Leu Pro Glu Leu Ile Gly Gly Ser Ala Asp Leu Thr
            370                 375                 380
Pro Ser Asn Leu Thr Arg Trp Glu Gly Ala Val Asp Phe Gln Pro Pro
385                 390                 395                 400
Ile Thr Gln Leu Gly Asn Tyr Ala Gly Arg Tyr Ile Arg Tyr Gly Val
                    405                 410                 415
Arg Glu His Gly Met Gly Ala Ile Met Asn Gly Ile Ser Ala Phe Gly
                    420                 425                 430
Ala Asn Tyr Lys Pro Tyr Gly Gly Thr Phe Leu Asn Phe Val Ser Tyr
            435                 440                 445
Ala Ala Gly Ala Val Arg Leu Ala Ala Leu Ser Gly Asn Pro Val Ile
450                 455                 460
Trp Val Ala Thr His Asp Ser Ile Gly Leu Gly Glu Asp Gly Pro Thr
465                 470                 475                 480
His Gln Pro Ile Glu Thr Leu Ala His Leu Arg Ala Ile Pro Asn Met
                    485                 490                 495
His Val Trp Arg Pro Ala Asp Gly Asn Glu Thr Ser Ala Ala Tyr Tyr
                    500                 505                 510
Ser Ala Ile Lys Ser Gly Arg Thr Pro Ser Val Val Ala Leu Ser Arg
            515                 520                 525
Gln Asn Leu Pro Gln Leu Glu His Ser Ser Phe Glu Lys Ala Leu Lys
            530                 535                 540
Gly Gly Tyr Val Ile His Asp Val Glu Asn Pro Asp Ile Ile Leu Val
545                 550                 555                 560
Ser Thr Gly Ser Glu Val Ser Ile Ser Ile Asp Ala Ala Lys Lys Leu
                    565                 570                 575
Tyr Asp Thr Lys Lys Ile Lys Ala Arg Val Val Ser Leu Pro Asp Phe
            580                 585                 590
Tyr Thr Phe Asp Arg Gln Ser Glu Glu Tyr Arg Phe Ser Val Leu Pro
            595                 600                 605
```

-continued

```
Asp Gly Val Pro Ile Met Ser Phe Glu Val Leu Ala Thr Ser Ser Trp
    610             615             620

Gly Lys Tyr Ala His Gln Ser Phe Gly Leu Asp Glu Phe Gly Arg Ser
625             630             635             640

Gly Lys Gly Pro Glu Ile Tyr Lys Leu Phe Asp Phe Thr Ala Asp Gly
            645             650             655

Val Ala Ser Arg Ala Glu Lys Thr Ile Asn Tyr Tyr Lys Gly Lys Gln
        660             665             670

Leu Leu Ser Pro Met Gly Arg Ala Phe
        675             680
```

MODIFIED TRANSKETOLASE AND USE THEREOF

CROSS REFERENCES TO RELATED APPLICATIONS

This application is a continuation of application Ser. No. 12/091,279 filed Jun. 12, 2008 now U.S. Pat. No. 8,257,944 which is a 371 of PCT/EP2006/010270 filed Oct. 25, 2006, which claims priority to European Patent Application No. 05023813.8 filed Nov. 2, 2005, the entire contents of each of which are hereby incorporated by reference.

The instant application contains a Sequence Listing which was submitted in the parent application in ASCII format via EFS-Web and is hereby incorporated by reference in its entirety. Said ASCII copy, created on Aug. 2, 2011, is named 4662-788.txt and is 67.628 bytes in size.

The present invention provides modified transketolase enzymes. Microorganisms synthesizing one of the modified transketolases instead of the wild type transketolase are prototroph for aromatic amino acids and impaired in using carbon sources that are assimilated via the pentose phosphate pathway. The modified enzymes and polynucleotides encoding the same can be used in the fermentation process for substances that use ribose-5-phosphate, ribulose-5-phosphate, or xylulose-5-phosphate as substrate for the biosynthesis such as e.g. riboflavin, riboflavin precursors, flavin mononucleotide (FMN), flavin adenine dinucleotide (FAD), and derivatives thereof. They also can be used for the production of pyridoxal phosphate (vitamin $B_6$), guanosine and adenosine and derivatives of these nucleotides.

BACKGROUND OF THE INVENTION

Riboflavin (vitamin $B_2$) is synthesized by all plants and many microorganisms but is not produced by higher animals. Because it is a precursor to coenzymes such as flavin adenine dinucleotide and flavin mononucleotide that are required in the enzymatic oxidation of carbohydrates, riboflavin is essential to basic metabolism. In higher animals, insufficient riboflavin can cause loss of hair, inflammation of the skin, vision deterioration, and growth failure.

The enzymes required catalyzing the biosynthesis of riboflavin from guanosine triphosphate (GTP) and ribulose-5-phosphate are encoded by four genes (ribG, ribB, ribA, and ribH) in *B. subtilis*. These genes are located in an operon, the gene order of which differs from the order of the enzymatic reactions catalyzed by the enzymes. For example, GTP cyclohydrolase II, which catalyzes the first step in riboflavin biosynthesis, is encoded by the third gene in the operon, ribA. The ribA gene also encodes a second enzymatic activity, i.e., 3,4-dihydroxy-2-butanone 4-phosphate synthase (DHBPS), which catalyzes the conversion of ribulose-5-phosphate to the four-carbon unit 3,4-dihydroxy-2-butanone 4-phosphate (DHBP). Deaminase and reductase are encoded by the first gene of the to operon, ribG. The penultimate step in riboflavin biosynthesis is catalyzed by lumazine synthase, the product of the last rib gene, ribH. Riboflavin synthase, which controls the last step of the pathway, is encoded by the second gene of the operon, ribB. The function of the gene located at the 3' end of the rib operon is, at present, unclear; however, its gene product is not required for riboflavin synthesis.

Transcription of the riboflavin operon from the ribP1 promoter is controlled by an attenuation mechanism involving a regulatory leader region located between ribP1 and ribG. ribO mutations within this leader region result in deregulated expression of the riboflavin operon. Deregulated expression is also observed in strains containing missense mutations in the ribC gene. The ribC gene has been shown to encode the flavin kinase/FAD synthase of *B. subtilis* (Mack, M., et al., J. Bacteriol., 180:950-955, 1998). Deregulating mutations reduce the flavokinase activity of the ribC gene product resulting in reduced intracellular concentrations of flavin mononucleotide (FMN), the effector molecule of the riboflavin regulatory system.

Engineering of riboflavin production strains with increased production rates and yields of riboflavin has been achieved in the past in a number of different ways. For instance, (1) classical mutagenesis was used to generate variants with random mutations in the genome of the organism of choice, followed by selection for higher resistance to purine analogs and/or by screening for increased production of riboflavin. (2) Alternatively, the terminal enzymes of riboflavin biosynthesis, i.e., the enzymes catalyzing the conversion of guanosine triphosphate (GTP) and ribulose-5-phosphate to riboflavin, were over-expressed, resulting also in a higher flux towards the target product. The metabolic flux into and through a biosynthetic pathway, e.g. the riboflavin biosynthetic pathway, is determined by the specific activities of the rate-limiting enzymes of this particular pathway and by the intracellular concentrations of the substrates for these enzymes. Only at or above saturating substrate concentrations an enzyme can operate at its maximal activity. The saturating substrate concentration is a characteristic feature for each enzyme. For example, the metabolic flux into the riboflavin pathway may be increased or kept at a high level by keeping the intracellular concentrations of ribulose-5-phophate above or as close as possible to the saturating substrate concentration of the 3,4-dihydroxy-2-butanone 4-phosphate synthase, a presumed rate limiting enzyme for the riboflavin biosynthetic pathway. High intracellular concentrations of ribulose-5-phosphate may, for example, be reached by preventing or interfering with drainage of ribulose-5-phosphate into the central metabolism via the non-oxidative part of the pentose phosphate pathway.

A key enzyme in the non-oxidative part of the pentose phosphate pathway is the transketolase enzyme, which catalyzes the reversible conversion of ribose-5-phosphate and xylulose-5-phosphate to seduheptulose-7-phosphate and glyceraldehyde-3-phosphate. In addition, transketolase catalyzes also the conversion of fructose-6-phosphate and glyceraldehyde-3-phosphate to xylulose-5-phosphate and erythrose-4-phosphate (Kochetov, G. A. 1982, Transketolase from yeast, rat liver, and pig liver, Methods Enzymol., 90:209-23).

SUMMARY OF THE INVENTION

It has previously been reported that transketolase deficient *Bacillus subtilis* strains carrying knock-out mutations in the transketolase encoding gene produces ribose, which accumulates in the fermentation broth (De Wulf, P., and E. J. Vandamme. 1997. Production of D-ribose by fermentation, Appl. Microbiol. Biotechnol. 48:141-148; Sasajima, K., and Yoneda, M. 1984, Production of pentoses by microorganisms. Biotechnol. and Genet. Eng. Rev. 2: 175-213). Obviously, increased intracellular C5 carbon sugar pools can be reached in transketolase knock-out mutants up to a level that exceeds the physiological requirements of the bacteria and leads to secretion of excess ribose.

As mentioned above, transketolase catalysed reactions are also required to produce erythrose-4-phosphate, from which the three proteinogenic aromatic amino acids are derived. Therefore, transketolase deficient microorganisms are auxotroph for these amino acids. They can only grow if these amino acids or their biosynthetic precursors, for instance shikimic acid, can be supplied via the cultivation medium.

In addition to the unfavorable auxotrophy for aromatic amino acids or shikimic acid, transketolase-deficient *B. subtilis* mutants show a number of severe pleiotropic effects like very slow growth on glucose, a defective phosphoenolpyruvate-dependent phosphotransferase system, deregulated carbon catabolite repression, and altered cell membrane and cell wall composition (De Wulf, P., and E. J. Vandamme. 1997).

An other transketolase-deficient riboflavin secreting *B. subtilis* strain was described by Gershanovich et al. (Gershanovich V N, Kukanova A Ia, Galushkina Z M, Stepanov A I (2000) Mol. Gen. Mikrobiol. Virusol. 3:3-7).

Furthermore, U.S. Pat. No. 6,258,554 B1 discloses a riboflavin overproducing *Corynebacterium glutamicum* strain in which transketolase activity is deficient. It can be noted form the disclosure of the U.S. Pat. No. 6,258,554 B1 that the deficiency in transketolase activity and the resulting amino acid auxotrophy was essential for the improved riboflavin productivity, since a prototrophic revertant produced riboflavin in amounts similar to a *C. glutamicum* strain with a wild-type transketolase background.

These disadvantages, i.e. auxotrophy for aromatic amino acids and further pleiotropic effects discussed above, make a transketolase deficient mutant a less preferable production strain for stable industrial processes, such as, e.g. the industrial production of riboflavin within such strain.

It is in general an object of the present invention to provide a transketolase mutant strain which is modified in such a way that the catalytic properties of the modified transketolase allowing higher intracellular ribulose-5-phosphate and ribose-5-phosphate concentrations than those of the non-modified transketolase, but which does not have the disadvantages of the transketolase-deficient strains mentioned above.

Surprisingly, it has now been found that by genetically altering a microorganism such as for instance *B. subtilis*, by replacing the wild-type gene by a mutated gene encoding a modified transketolase that allows some residual flux through the pentose phosphate pathway by having modulated specific activities, the production of a fermentation product such as e.g. riboflavin can be significantly improved without loosing the prototrophic properties.

The present invention relates to modified transketolases, polynucleotide sequences comprising a gene that encodes a modified transketolase with properties described above, a host cell which has been transformed by such a polynucleotide sequence, and a process for the biotechnological production of a fermentation product such as for instance riboflavin, a riboflavin precursor, FMN, FAD, pyridoxal phosphate or one or more derivatives thereof based on a host cell in which the wild-type transketolase gene has been stably replaced by a polynucleotide coding for the mutated transketolase.

As a first step to isolate mutants, in which the wild-type transketolase is replaced by one of such modified transketolases, a deletion mutant may be generated that is auxotroph for the proteinogenic aromatic amino acids and cannot grow with carbon sources assimilated via the pentose phosphate pathway, e.g. gluconate. The transketolase deletion mutant may then to be transformed with a mixture of DNA fragments encoding various transketolase mutants. Prototrophic transformants may be isolated, from which those are selected which show a reduced growth rate on gluconate. Mutants isolated according to this method may synthesize modified transketolase enzymes that allow sufficient erythrose-4-phosphate biosynthesis to prevent auxotrophic growth, but act as a bottle neck for assimilation of gluconate. In addition, the undesired pleiotropic effects typically observed with *B. subtilis* transketolase deletion mutants may be prevented. U.S. Pat. No. 6,258,554 B1 indicates that together with the reversion of the auxotrophic to the prototrophic growth riboflavin secreting *C. glutamicum* transketolase mutants lost their ability to produce more riboflavin than a similar strain containing a wild-type transketolase gene. As shown in the examples of the present invention, prototrophic *B. subtilis* transketolase mutants isolated as outlined above unexpectedly produced more riboflavin than the transketolase wild-type parent strain, whereas a transketolase deletion mutant had partly lost their riboflavin production capabilities.

Methods for the introduction of mutations into DNA fragments are well known in the art. Transketolase mutants can be generated for instance by protein engineering using one of the available 3D structures of e.g. the yeast transketolase (Lindqvist, Y., G. Schneider, U. Ermler, and M. Sundstrom. 1992. Three-dimensional structure of transketolase, a thiamine diphosphate dependent enzyme, at 2.5 A resolution. Embo. J. 11:2373-9) for selecting suitable positions of the amino acid sequence or by random mutagenesis. The selection process in both cases may be done as described above. The modified transketolase—when it is used as substitution for the wild-type transketolase—exhibits catalytic properties, i.e. modulated specific activities, which allow the growth of a host cell on a carbon source that is metabolized exclusively by the pentose phosphate pathway (for example gluconate) with a reduced growth rate in comparison to a host cell containing the wild-type transketolase. These properties result in higher intracellular ribulose-5-phosphate and ribose-5-phosphate concentrations and a residual flux through the pentose phosphate pathway, so that sufficient erythrose-4-phosphate can be produced to prevent auxotrophic growth.

"Wild-type enzyme" or "wild-type transketolase" which can be used for the present invention may include any transketolase as defined above that is used as starting point for designing mutants according to the present invention. The wild-type transketolase may be of eukaryotic or prokaryotic, preferably fungal or bacterial origin, in particular selected from *Escherichia*, *Bacillus*, *Corynebacterium*, *Saccharomyces*, *Eremothecium*, *Candida* or *Ashbya*, preferably from *E. coli*, *B. subtilis*, *B. licheniformis*, *B. halodurans*, *S. cerevisiae*, *E. gossypii*, *C. flareri* or *A. gossypii* or any transketolase having an amino acid sequence which is homologous to an amino acid sequence as shown in FIG. 1. Most preferably the transketolase is from *B. subtilis*. "Homologous" refers to a transketolase that is at least about 50% identical, preferably at least about 60% identical, more preferably at least about 70%, 80%, 85%, 90%, 95% identical, and most preferably at least about 98% identical to one or more of the amino acid sequences as shown in FIG. 1. "Wild-type" in the context of the present invention may include both transketolase sequences derivable from nature as well as variants of synthetic transketolase enzymes (as long as they are homologous to any one of the sequences shown in FIG. 1), The terms "wild-type transketolase" and "non-modified transketolase" are used interchangeably herein.

The term "% identity", as known in the art, means the degree of relatedness between polypeptide or polynucleotide sequences, as the case may be, as determined by the match between strings of such sequences. "Identity" can be readily determined by known methods, e.g., with the program BEST-FIT (GCG Wisconsin Package, version 10.2, Accelrys Inc., 9685 Scranton Road, San Diego, Calif. 92121-3752, USA) using the following parameters: gap creation penalty 8, gap extension penalty 2 (default parameters).

A "mutant", "mutant enzyme", "mutated enzyme" or "mutant transketolase" or a "modified transketolase" as used herein means any variant derivable from a given wild-type enzyme/transketolase (according to the above definition) according to the teachings of the present invention and, when used for replacing the wild-type gene of a host organism/cell should have an effect on the growth on e.g. gluconate and/or ribose. For the scope of the present invention, it is not relevant how the mutant(s) are obtained; such mutants may be obtained, e.g., by site-directed mutagenesis, saturation mutagenesis, random mutagenesis/directed evolution, chemical or UV mutagenesis of entire cells/organisms, etc. These mutants may also be generated, e.g., by designing synthetic genes, and/or produced by in vitro (cell-free) translation. For testing of specific activity, mutants can may be (over-)expressed by methods known to those skilled in the art. The terms "mutant transketolase", "modified transketolase" or "mutated transketolase" are used interchangeably herein.

"Host cell" is a cell capable of producing a given fermentation product and containing the wild-type transketolase, or a nucleic acid encoding the modified transketolase according to the invention. Suitable host cells include cells of microorganisms.

As used herein, the term "specific activity" denotes the reaction rate of the wild-type and mutant transketolase enzymes under properly defined reaction conditions as described in Kochetov (Kochetov, G. A. 1982. Transketolase from yeast, rat liver, and pig liver. Methods Enzymol 90:209-23). The "specific activity" defines the amount of substrate consumed and/or product produced in a given time period and per defined amount of protein at a defined temperature. Typically, "specific activity" is expressed in µmol substrate consumed or product formed per min per mg of protein. Typically, µmol/min is abbreviated by U (=unit). Therefore, the unit definitions for specific activity of µmol/min/(mg of protein) or U/(mg of protein) are used interchangeably throughout this document. It is understood that in the context of the present invention, specific activity must be compared on the basis of a similar, or preferably identical, length of the polypeptide chain.

Many mutations may change a wild-type transketolase in such a way that growth on gluconate is affected as described above.

It is an object of the present invention to provide a modified transketolase having the properties defined above, wherein the amino acid sequence of the modified transketolase contains at least one mutation when compared with the amino acid sequence of the corresponding non-modified transketolase.

The at least one mutation may be an addition, deletion and/or substitution.

Preferably, the at least one mutation is at least one amino acid substitution wherein a given amino acid present in the amino acid sequence of the non-modified transketolase is replaced with a different amino acid in the amino acid sequence of the modified transketolase of the invention. The amino acid sequence of the modified transketolase may contain at least one amino acid substitution when compared with the amino acid sequence of the corresponding non-modified transketolase. Particularly, a modified transketolase as of the present invention contains at least one mutation on an amino acid position which corresponds to amino acid position 357 of the B. subtilis transketolase amino acid sequence as depicted in SEQ ID NO:2.

In further embodiments, the modified transketolase contains at least two, at least three, at least four or at least five substitutions when compared with the amino acid sequence of the corresponding transketolase. For example, the modified transketolase contains one to ten, one to seven, one to five, one to four, two to ten, two to seven, two to five, two to four, to three to ten, three to seven, three to five or three to four amino acid substitutions when compared with the amino acid sequence of the corresponding non-modified transketolase.

In a preferred embodiment of the invention the non-modified transketolase is obtainable from Bacillus, preferably B. subtilis, as depicted in SEQ ID NO:2. The corresponding DNA sequence is shown in SEQ ID NO:1. The modified transketolase contains at least one mutation on position 357 of SEQ ID NO:2, leading to a modified transketolase having the above described properties.

The at least one amino acid substitution in the non-modified transketolase located on a position corresponding to amino acid 357 as shown in SEQ ID NO:2 may be selected from substitution R357H, R357A, R357S, R357N, R357T, R357K, R357I, R357V, R357G, and R357L.

In a particularly preferred embodiment, the mutated transketolase consists of one substitution which affects the amino acid position corresponding to amino acid position 357 of the amino acid sequence as shown in SEQ ID NO:2 and which may be selected from substitution R357H, R357A, R357S, R357N, R357T, R357K, R357I, R357V, R357G, and R357L.

In an other preferred embodiment, the modified transketolase contains at least two amino acid substitutions when compared with the amino acid sequence of the corresponding non-modified transketolase, wherein at least one mutation corresponding to amino acid position 357 of the amino acid sequence as shown in SEQ ID NO:2 and which may be selected from substitution R357H, R357A, R357S, R357N, R357T, R357K, R357I, R357V, R357G, and R357L.

The amino acid present in the non-modified transketolase is preferably arginine at position 357. The amino acid in the sequence of the non-modified transketolase may be changed to histidine, alanine, serine, asparagine, lysine, threonine, leucine, glycine, isoleucine or valine at position 357. Preferably, the substitution at the amino acid position corresponding to position 357 of the sequence as shown in SEQ ID NO: 2 consists of the replacement of arginine with histidine, arginine with alanine, arginine with serine, arginine with leucine, arginine with lysine, arginine with asparagine, arginine with threonine, arginine with glycine, arginine with isoleucine, arginine with valine.

The modified transketolase of the invention may comprise foreign amino acids, preferably at its N- or C-terminus "Foreign amino acids" mean amino acids which are not present in a native (occurring in nature) transketolase, preferably a stretch of at least about 3, at least about 5 or at least about 7 contiguous amino acids which are not present in a native transketolase. Preferred stretches of foreign amino acids include but are not limited to "tags" that facilitate purification of the recombinantly produced modified transketolase. Examples of such tags include but are not limited to a "His6" tag (SEQ ID NO: 31), a FLAG tag, a myc tag, and the like. For calculation of specific activity, the values need to be corrected for these additional amino acids (see also above).

In another embodiment the modified transketolase may contain one or more, e.g. two, deletions when compared with the amino acid sequence of the corresponding non-modified transketolase. Preferably, the deletions affect N- or C-terminal amino acids of the corresponding non-modified transketolase and do not significantly reduce the functional properties, e.g., the specific activity, of the enzyme.

The invention further relates to a polynucleotide comprising a nucleotide sequence which codes for a modified transketolase according to the invention. "Polynucleotide" as used herein refers to a polyribonucleotide or polydeoxyribonucleotide that may be unmodified RNA or DNA or modified RNA or DNA. Polynucleotides include but are not limited to single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. The term "polynucleotide" includes DNA or RNA that comprises one or more unusual bases, e.g., inosine, or one or more modified bases, e.g., tritylated bases.

The polynucleotide of the invention can easily be obtained by modifying a polynucleotide sequence which codes for a non-modified transketolase. Examples of such polynucleotide sequences encoding non-modified transketolase enzymes include but are not limited to the amino acid sequences of FIG. 1. Preferably, the non-modified transketolase is originated from *Bacillus*, in particular *B. subtilis*, more preferred is a polynucleotide encoding a non-modified transketolase as depicted in SEQ ID NO:2.

Methods for introducing mutations, e.g., additions, deletions and/or substitutions into the nucleotide sequence coding for the non-modified transketolase include but are not limited to site-directed mutagenesis and PCR-based methods.

DNA sequences of the present invention may be constructed starting from genomic or cDNA sequences coding for transketolase enzymes known in the state of the art, as are available from, e.g., Genbank (Intelligenetics, California, USA), European Bioinformatics Institute (Hinston Hall, Cambridge, GB), NBRF (Georgetown University, Medical Centre, Washington, D.C., USA) and Vecbase (University of Wisconsin, Biotechnology Centre, Madison, Wis., USA) or from the sequence information disclosed in FIG. 1 by methods of in vitro mutagenesis [see e.g. Sambrook et al., Molecular Cloning, Cold Spring Harbor Laboratory Press, New York]. Another possibility of mutating a given DNA sequence which may also be suitable for the practice of the present invention is mutagenesis by using the polymerase chain reaction (PCR). DNA as starting material may be isolated by methods known in the art and described, e.g., in Sambrook et al. (Molecular Cloning) from the respective strains/organisms. It is, however, understood that DNA encoding a transketolase to be constructed/mutated in accordance with the present invention can also be prepared on the basis of a known DNA sequence, e.g. by construction of a synthetic gene by methods known in the art (as described, e.g., in EP 747483).

Once complete DNA sequences of the present invention have been obtained, they can be integrated into vectors or directly introduced into the genome of a host organism by methods known in the art and described in, e.g., Sambrook et al. (s.a.) to (over-) express the encoded polypeptide in appropriate host systems. However, a man skilled in the art knows that also the DNA sequences themselves can be used to transform the suitable host systems of the invention to get (over-) expression of the encoded polypeptide.

In a preferred embodiment the present invention provides (i) a DNA sequence which codes for a modified transketolase carrying at least one mutation as defined above and which hybridizes under standard conditions with any of the DNA sequences of the specific modified transketolase enzymes, for example which hybridizes with the DNA sequences according to SEQ ID NO:1, or (ii) a DNA sequence which codes for a modified transketolase carrying at least one mutation as defined above but, because of the degeneracy of the genetic code, does not hybridize but which codes for a polypeptide with exactly the same amino acid sequence as a DNA sequence which hybridizes under standard conditions with any of the DNA to sequences of the specific modified transketolase enzymes of the present invention, or (iii) a DNA sequence which is a fragment of such modified DNA sequences which maintains the activity properties of the polypeptide of which it is a fragment.

"Standard conditions" for hybridization mean in the context of the present invention the conditions which are generally used by a man skilled in the art to detect specific hybridization signals and which are described, e.g. by Sambrook et al., "Molecular Cloning", second edition, Cold Spring Harbor Laboratory Press 1989, New York, or preferably so-called stringent hybridization and non-stringent washing conditions or more preferably so-called stringent hybridization and stringent washing conditions a man skilled in the art is familiar with and which are described, e.g., in Sambrook et al. (s.a.). A specific example of stringent hybridization conditions is overnight incubation (e.g., 15 hours) at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 µg/ml of denatured, sheared salmon sperm DNA, followed by washing the hybridization support in 0.1×SSC at about 65° C.

In another preferred embodiment the invention further provides a DNA sequence which can be obtained by the so-called polymerase chain reaction method ("PCR") by PCR primers as shown in FIG. 2, designed on the basis of the specifically described DNA sequences.

The polypeptides and polynucleotides of the present invention are preferably provided in an isolated form, and preferably purified to homogeneity.

The term "isolated" means that the material is removed from its original environment (e.g., the natural environment if it is naturally occurring). For example, a naturally-occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

An isolated polynucleotide or nucleic acid as used herein may be a DNA or RNA that is not immediately contiguous with both of the coding sequences with which it is immediately contiguous (one on the 5'-end and one on the 3'-end) in the naturally occurring genome of the organism from which it is derived. Thus, in one embodiment, a to nucleic acid includes some or all of the 5'-non-coding (e.g., promoter) sequences that are immediately contiguous to the coding sequence. The term "isolated polynucleotide" therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the term isolated polypeptide refers to a polypeptide that is substantially free of other polypeptides.

An isolated polypeptide is preferably greater than 80% pure, more preferably greater than 90% pure, even more preferably greater than 95% pure, most preferably greater than 99% pure. Purity may be determined according to methods known in the art, e.g., by SDS-PAGE and subsequent protein staining. Protein bands can then be quantified by densitometry. Further methods for determining the purity are within the level of ordinary skill.

As mentioned above, the modified transketolases and the corresponding polynucleotides of the invention may be utilized in the genetic engineering of a suitable host cell to make it better and more efficient in the fermentation process for substances that use ribose-5-phosphate, ribulose-5-phosphate, or xylulose-5-phosphate as substrate for the biosynthesis. The presence of said modified transketolase within a suitable host cell may result in higher intracellular ribulose-5-phosphate and ribose-5-phosphate concentrations and a residual flux through the pentose phosphate pathway within said recombinant host, so that sufficient erythrose-4-phosphate can be produced to prevent auxotrophic growth.

Appropriate host cells are for example fungi, like Aspergilli, e.g. Aspergillus niger or Aspergillus oryzae, or like Trichoderma, e.g. Trichoderma reesei, or Ashbya, e.g. Ashbya gossypii, or Eremothecium, e.g. Eremothecium ashbyii, or yeasts like Saccharomyces, e.g. Saccharomyces cerevisiae, or Candida, like Candida flareri, or Pichia, like Pichia pastoris, or Hansenula polymorpha, e.g. H. polymorpha (DSM 5215). Bacteria which can be used are, e.g., Bacilli as, e.g., Bacillus subtilis or Streptomyces, e.g. Streptomyces lividans. E. coli which could be used are, e.g., E. coli K12 strains, e.g. M15 or HB 101.

Thus, the present invention relates to a microorganism wherein the activity of a transketolase is modified in such a way that the microorganism is capable of growing on a carbon source that is metabolized exclusively by the pentose phosphate pathway (for example gluconate) with a reduced growth rate in comparison to a host cell containing the wild-type transketolase. It is in general possible to introduce an obtained transketolase mutant originating from a certain organism e.g. B. subtilis in the same organism again and now used as a host cell or to introduce any obtained mutant into any other relevant host cells.

As used herein, the term "growth rate" denotes to the following: Bacterial cells reproduce by dividing in two. If growth is not limited, doubling continues at a constant rate so both the number of cells and the rate of population increase doubles with each consecutive time period. For this type of exponential growth, plotting the natural logarithm of cell number against time (preferably in hours) produces a straight line. The slope of this line is the specific growth rate of the organism, which is a measure of the number of divisions per cell per unit time. In food, bacteria cannot grow continuously as the amount of nutrient available will be finite and waste products will accumulate. In these conditions growth curves tend to be sigmoid.

It is an object of the present invention to provide a recombinant host cell wherein the growth rate of said recombinant host cell (e.g. microorganism) according to the present invention carrying a modified transketolase on a carbon source that is metabolized exclusively by the pentose phosphate pathway, in particular gluconate, is less than 100% when compared to the wild-type organism. In particular, the growth rate may be reduced by at least 10%, 20%, 30%, 40%, 50%, 60%, 70%, 80% or even 90% and more compared to the growth rate of a wild-type organism. Preferably, the growth rate reduction is between 10% and 90%, more preferably between 20% and 80%, still more preferably between 25% and 75% compared to a cell containing a wild-type transketolase gene.

Especially, the invention relates to a genetically engineered/recombinantly produced host cell (also referred to as recombinant cell or transformed cell) in which the wild-type transketolase gene has been replaced by a modified transketolase gene encoding an enzyme that allows a slightly or non-reduced growth on a carbon source that is not exclusively metabolized by the pentose phosphate pathway, but shows a clearly reduced growth rate to when the organism grows on a carbon source that is metabolized exclusively by the pentose phosphate pathway. Such genetically engineered host cells show an improvement of the yield of the fermentation product and of the efficiency of the production process with the advantages that undesired auxotrophic growth and pleiotropic effects can be prevented.

The invention further relates to a process for producing a host cells capable of expressing a transketolase according to the invention, comprising the steps of (i) generating mutated transketolases displaying modulated activities in comparison to the respective wild-type enzyme, i.e.
  a) providing a polynucleotide encoding a first or non-modified transketolase with catalytic properties that should be adapted;
  b) introducing one or more mutations into the polynucleotide sequence such that the mutated polynucleotide sequence encodes a new or modified transketolase which contains at least one amino acid mutation when compared to the first transketolase wherein the at least one amino acid mutation may be at amino acid corresponding to position 357 of the amino acid sequence as shown in SEQ ID NO: 2;
  c) optionally inserting the mutated polynucleotide in a vector or plasmid;
(ii) replacing the wild-type transketolase(s) of the host cell by a transketolase variant from the same organisms or another organism that allows normal or slightly reduced growth on a carbon source that is not exclusively metabolized by the pentose phosphate pathway, but shows an effect on the growth rate when the organism grows on a carbon source that is metabolized exclusively by the pentose phosphate pathway, i.e.
  a) replacing the wild-type transketolase of a suitable wild-type host cell without altering the regulatory sequences of the gene;
  b) determining the growth rate on gluconate in minimal medium and comparing it to the wild-type host strain; and
  c) selecting transketolase mutants that allow a growth rate on gluconate which is less than 100% of the wild-type strain.

The invention further relates to a method for the production of substances that are secondary products of ribose-5-phosphate, ribulose-5-phosphate, or xylulose-5-phosphate comprising:
  a) culturing a genetically engineered/recombinantly produced host cell in which the wild-type transketolase gene has been replaced by a modified transketolase gene encoding an enzyme that allows a slightly or non-reduced growth on a carbon source that is not exclusively metabolized by the pentose phosphate pathway, but which shows a reduced growth rate when the organism grows on a carbon source that is metabolized exclusively by the pentose phosphate pathway, in a suitable medium under conditions that allow expression of the modified transketolase; and b) separating the fermentation product from the medium.

The "fermentation product" as used herein may be any product produced by a suitable host cell as defined above the biosynthesis of which uses ribose-5-phosphate, ribulose-5-phosphate, or xylulose-5-phosphate as substrate. Examples of such fermentation products include but are not limited to riboflavin, riboflavin precursors, flavin mononucleotide (FMN), flavin adenine dinucleotide (FAD) and derivatives thereof, pyridoxal phosphate (vitamin $B_6$), guanosine, adenosine and derivatives of these nucleotides.

"Riboflavin precursor" and "derivatives of riboflavin, FMN or FAD" in the context of this invention shall include any and all metabolite(s) requiring ribulose-5-phosphate or ribulose-5-phosphate as an intermediate or substrate in their (bio-) synthesis. In the context of this patent application, it is irrelevant whether such (bio-) synthesis pathways are natural or non-natural (i.e., pathways not occurring in nature, but engineered biotechnologically). Preferably, the synthesis pathways are biochemical in nature. Riboflavin precursors and derivatives of riboflavin, FMN or FAD include but are not limited to: DRAPP; 5-amino-6-ribosylamino-2,4 (1H,3H)-pyrimidinedione-5'-phosphate; 2,5-diamino-6-ribitylamino-4(3H)-pyrimidinone-5'-phosphate; 5-amino-6-ribitylamino-2,4(1H,3H)-pyrimidinedione-5'-phosphate; 5-amino-6-ribitylamino-2,4(1H,3H)-pyrimidinedione; 6,7-dimethyl-8-ribityllumazine (DMRL); and flavoproteins. The term "riboflavin" also includes derivatives thereof, such as e.g. riboflavin-5-phosphate and salts thereof, such as e.g. sodium riboflavin-5-phosphate.

The polynucleotides, polypeptides, recombinant host cells and methods described herein may be used for the biotechnological production of either one or more of the fermentation products as defined above.

Methods of genetic and metabolic engineering of suitable host cells according to the present invention are known to the man skilled in the art. Similarly, (potentially) suitable purification methods for e.g. riboflavin, a riboflavin precursor, FMN, FAD, pyridoxal phosphate or one or more derivatives thereof are well known in the area of fine chemical to biosynthesis and production.

It is understood that a method for biotechnological production of a fermentation product such as for instance riboflavin, a riboflavin precursor, FMN, FAD, pyridoxal phosphate or one or more derivatives thereof according to the present invention is not limited to whole-cellular fermentation processes as described above, but may also use, e.g., permeabilized host cells, crude cell extracts, cell extracts clarified from cell remnants by, e.g., centrifugation or filtration, or even reconstituted reaction pathways with isolated enzymes. Also combinations of such processes are in the scope of the present invention. In the case of cell-free biosynthesis (such as with reconstituted reaction pathways), it is irrelevant whether the isolated enzymes have been prepared by and isolated from a host cell, by in vitro transcription/translation, or by still other means.

Fermentation media must contain suitable carbon substrates. Suitable substrates may include but are not limited to monosaccharides such as glucose or fructose, oligosaccharides such as lactose or sucrose, polysaccharides such as starch or cellulose or mixtures thereof and unpurified mixtures from renewable feedstocks. It is contemplated that the source of carbon utilized in the present invention may encompass a wide variety of carbon containing substrates and will only be limited by the choice of organism.

The various embodiments of the invention described herein may be cross-combined.

BRIEF DESCRIPTION OF THE DRAWINGS

The present invention will now be illustrated in more detail by the following non-limiting examples. These examples are described with reference to the Figures.

FIG. 1 shows—as already mentioned above—examples of polynucleotide sequences which code for a non-modified transketolase (SEQ ID NOS 32-40, respectively, in order of appearance), and FIG. 2 shows a set of primers, in which tkt 1S is SEQ ID NO:3, tkt 1AS is SEQ ID NO:13, tkt 1ASohne is SEQ ID NO:6, tkt 2S is SEQ ID NO:4, tkt 2AS is SEQ ID NO:4, tkt 3S is SEQ ID NO:9, tkt 4S is SEQ ID NO:10, tkt 5S is SEQ ID NO:11, tkt 6S is SEQ ID NO:12, tkt 357AS is SEQ ID NO:14, tkt Rec 1S is SEQ ID NO:27, tkt Rec 1AS is SEQ ID NO:28, tkt Rec 2S is SEQ ID NO:29, tkt Rec 2AS is SEQ ID NO:30, tkt 357A-S is SEQ ID NO:17, tkt 357N-S is SEQ ID NO:15, tkt 357K-S is SEQ ID NO:18, tkt 357Q-S is SEQ ID NO:16, tkt 357S-S is SEQ ID NO:19, tkt 357T-S is SEQ ID NO:20, tkt 357H-S is SEQ ID NO:21, tkt 357V-S is SEQ ID NO:22, tkt 357I-S is SEQ ID NO:23, tkt 357L-S is SEQ ID NO:24, tkt 357M-S is SEQ ID NO:25, tkt 357G-S is SEQ ID NO:26, rpi MutS is SEQ ID NO:5.

DETAILED DESCRIPTION OF PREFERRED EMBODIMENTS

In particular, FIG. 1 shows multiple sequence alignment calculated by the program clustalW (1.83) of the transketolase amino acid sequences from *Escherichia coli* (TKT_ECOLI), *Bacillus subtilis* (TKT_BACSU), *Bacillus licheniformis* (TKT_BACLD), *Bacillus halodurans* (TKT_BACHD), *Corynebacterium glutamicum* (TKT_CORGL), *Saccharomyces cerevisiae* (TKT_YEAST), and *Ashbya gossypii* (TKT_ASHGO). Positions that are homologous/equivalent to the amino acid residue 357 of the *B. subtilis* transketolase that are discussed in one of the following examples are in bold letters. The numbering used for those positions is done according to the *B. subtilis* wild-type amino acid sequence. This type of alignment can be done with CLUSTAL or PILEUP using standard parameters. As shown, the amino acid sequence of transketolases is highly conserved. In particular, in all transketolases shown and in much more transketolases not shown, arginine 357 (numbering according to the *B. subtilis* transketolase) is conserved. Therefore, the type of experiment using the concepts and mutations reported here can also be done with other transketolases having an arginine at a position homologous to position 357 of the amino acid sequence of *B. subtilis* transketolase like *Ashbya gossypii* for improving the production of riboflavin, riboflavin derivatives or compounds having ribose-5-phosphate, xylulose-5-phosphate, or ribulose-5-phosphate as a precursor. It is also possible to replace an original transketolase gene of an organism by a *B. subtilis* transketolase mutant gene mutated at position 357 with or without adaptation of the DNA sequence to the new organism. It is not essential that the transketolase mutant genes originate from an organism in which it is going to be introduced. The practical steps required for another host organism are published and known to an expert in the field and outlined somewhere else.

Example 1

Isolation of Genomic DNA from *Bacillus subtilis* gDNA was prepared using the DNeasy Tissue Kit from Qiagen (QIAGEN GmbH, QIAGEN Str. 1, 40724 Hilden, Germany) according to the description of the supplier. 1 ml of a 3 ml overnight culture of *B. subtilis* in VY liquid medium (Becton Dickinson, Sparks, Md. 21152, USA) incubated at 37° C. (250 rpm) was used as source for the bacteria cells. At the end, the gDNA was eluted in 200 µl of AE buffer (supplied with the Kit).

Example 2

Amplification of the Transketolase Gene from *Bacillus subtilis* gDNA from *B. subtilis* PY79 (P. Youngman, J. Perkins, and R. Losick (1984), Construction of a cloning site near one end of Tn917 into which foreign DNA may be inserted without affecting transposition in *Bacillus subtilis* or expression on the transposon-borne erm gene. Plasmid 12:1-9; see Example 1) was used for amplification of the tkt gene. According to the genomic DNA sequence, the tkt gene contains one Eco RI site inside of its coding sequence (SEQ ID NO: 1). Since the Eco RI restriction site is generally used for cloning into *E. coli* expression vectors such as pQE80 (QIAGEN GmbH, QIAGEN Str. 1, 40724 Hilden, Germany), the site was deleted by replacing C315 by a T, which is a silent mutation changing the phenylalanine codon from TTC to TTT. For this, two separate PCRs A and B were performed. The following PCR conditions were used for PCR A: 2 µM of primer tkt 1S (according to SEQ ID No: 3, see also FIG. 2) and tkt 2AS (according to SEQ ID No: 4, FIG. 2), 0.2 mM of each nucleotide (ATP, GTP, TTP, CTP), 2.5 U of a proof-reading DNA polymerase (Stratagene, Gebouw Calif., 1101 CB Amsterdam Zuidoost, The Netherlands), 100 ng genomic DNA (Example 1) in the appropriate buffer as supplied together with the DNA polymerase.

Temperature regulation was as follows:
Step 1: 3 min at 95° C.
Step 2: 30 sec at 95° C.
Step 3: 30 sec at 52° C.
Step 4: 30 sec at 72° C.
Step 5: 5 min at 72° C.
Steps 2 to 4 were repeated 35-times.

PCR B was done under the following conditions: 2 µM of primer tkt 2S (according to SEQ ID No: 8, FIG. 2) and tkt 1AS (according to SEQ ID No: 13, FIG. 2), 0.2 mM of each nucleotide (ATP, GTP, TTP, CTP), 2.5 U of a proof-reading DNA polymerase (Stratagene, Gebouw Calif., 1101 CB Amsterdam Zuidoost, The Netherlands), 100 ng genomic DNA (Example 1) in the appropriate buffer as supplied together with the DNA polymerase.

Temperature regulation was as follows:
Step 1: 3 min at 95° C.
Step 2: 30 sec at 95° C.
Step 3: 30 sec at 52° C.
Step 4: 2 min at 72° C.
Step 5: 5 min at 72° C.
Steps 2 to 4 were repeated 35-times.

The two PCR products A and B were purified by Agarose gel electrophoresis and a following extraction out of the gel using the MinElute Gel Extraction Kit from Qiagen (QIAGEN GmbH, QIAGEN Str. 1, 40724 Hilden, Germany). Using the overlapping region of PCR products A and B, it was possible to assemble them by a third PCR: 2 µM of primer Rpi MutS (according to SEQ ID No: 5, FIG. 2) and tkt 1ASohne (according to SEQ ID No: 6, FIG. 2), 0.2 mM of each nucleotide (ATP, GTP, TTP, CTP), 2.5 U of a proof-reading DNA polymerase (Stratagene, Gebouw Calif., 1101 CB Amsterdam Zuidoost, The Netherlands), 100 ng of PCR product A and PCR product B in the appropriate buffer as supplied together with the DNA polymerase.

Step 1: 3 min at 95° C.
Step 2: 30 sec at 95° C.
Step 3: 30 sec at 53° C.
Step 4: 2.5 min at 72° C.
Step 5: 5 min at 72° C.
Steps 2 to 4 were repeated 35-times.

The PCR products were purified with the help of the Qiagen PCR purification Kit (QIAGEN GmbH, QIAGEN Str. 1, 40724 Hilden, Germany) and eluted in 50 µl elution buffer. The PCR product was confirmed by an Eco RI digestion. For further confirmation, it was sequenced with the primers tkt 1S, tkt 2S, tkt 2AS, tkt 3S (according to SEQ ID No: 9, FIG. 2), tkt 4S (according to SEQ ID No: 10, FIG. 2), tkt 5S (according to SEQ ID No: 11, FIG. 2), tkt 6S (according to SEQ ID No: 12, FIG. 2), tkt 1AS.

Example 3

Construction of tkt Mutants

The 3D structure of the yeast transketolase was available together with a selection of mutations that showed influence on substrate binding of the yeast transketolase (Nilsson, U., L. Meshalkina, Y. Lindqvist, and G. Schneider. 1997. At position R359 (number 357 in the *B. subtilis* transketolase), the original arginine was replaced by nearly all other amino acids. The construction of the mutants was basically done as described in example 1. An amino acid sequence alignment comprising the transketolases from yeast, *B. subtilis* and from other organisms is shown in FIG. 1.

Using the Eco RI-free tkt gene as template (Example 2), the mutations were introduced as already described for the deletion of the Eco RI site: The following PCR conditions were used for PCR A and B: 2 µM of primer Rpi MutS (A) or tkt 357nnn-S (B) and tkt 357AS (A) (according to SEQ ID No: 14, FIG. 2) or tkt 1ASohne (B), 0.2 mM of each nucleotide (ATP, GTP, TTP, CTP), 2.5 U of a proof-reading DNA polymerase (Stratagene, Gebouw Calif., 1101 CB Amsterdam Zuidoost, The Netherlands), 100 ng of the Eco RI-free tkt gene (Example 2) in the appropriate buffer as supplied together with the DNA polymerase. In the case of PCR B the sense primer was chosen according to the amino acid that was introduced: tkt 357N-S (according to SEQ ID No: 15, FIG. 2) for asparagine, tkt 357Q-S (according to SEQ ID No: 16, FIG. 2) for glutamine, tkt 357A-S (according to SEQ ID No: 17, FIG. 2) for alanine, tkt 357K-S (according to SEQ ID No: 18, FIG. 2) for lysine, tkt 357S-S (according to SEQ ID No: 19, FIG. 2) for serine, tkt 357T-S (according to SEQ ID No: 20, FIG. 2) for threonine, tkt 357H-S (according to SEQ ID No: 21, FIG. 2) for histidine, tkt 357V-S (according to SEQ ID No: 22, FIG. 2) for valine, tkt 357I-S (according to SEQ ID No: 23, FIG. 2) for Isoleucine, tkt 357L-S (according to SEQ ID No: 24, FIG. 2) for leucine, tkt 357M-S (according to SEQ ID No: 25, FIG. 2) for methionine, and tkt 357G-S (according to SEQ ID No: 26, FIG. 2) for the introduction of glycine at position 357 of the *B. subtilis* transketolase.

Temperature regulation was as follows:
Step 1: 3 min at 95° C.
Step 2: 30 sec at 95° C.
Step 3: 30 sec at 52° C.
Step 4: 60 sec at 72° C.
Step 5: 5 min at 72° C.
Steps 2 to 4 were repeated 35-times.

The two PCR products A and B were purified by Agarose gel electrophoresis and a following extraction out of the gel using the MinElute Gel Extraction Kit from Qiagen (QIAGEN GmbH, QIAGEN Str. 1, 40724 Hilden, Germany). Assembling of PCR product A and B was done in a third PCR: 2 μM of primer Rpi MutS and tkt 1ASohne, 0.2 mM of each nucleotide (ATP, GTP, TTP, CTP), 2.5 U of a proof-reading DNA polymerase (Stratagene, Gebouw Calif., 1101 CB Amsterdam Zuidoost, The Netherlands), 100 ng of PCR product A and PCR product B in the appropriate buffer as supplied together with the DNA polymerase.

Step 1: 3 min at 95° C.
Step 2: 30 sec at 95° C.
Step 3: 30 sec at 53° C.
Step 4: 2.5 min at 72° C.
Step 5: 5 min at 72° C.
Steps 2 to 4 were repeated 35-times.

The PCR products of the transketolase were purified with the Qiagen PCR purification Kit (QIAGEN GmbH, QIAGEN Str. 1, 40724 Hilden, Germany) and eluted in 50 μl elution buffer. The PCR products were used for the transformation of B. subtilis.

Example 4

Construction of a Transketolase-Deficient B. subtilis Strain

For the marker free introduction of a mutated transketolase gene into the original tkt locus of the B. subtilis genome, a transketolase-deficient strain was constructed. Two DNA fragments obtained by PCR comprising base pair 452 to 1042 and base pair 1562 to 2001 of the B. subtilis transketolase gene (SEQ ID NO: 2) were combined with the neomycin resistance gene cassette (M. Itaya, K. Kondo, and T. Tanaka. 1989. A neomycin resistance gene cassette selectable in a single copy state in the Bacillus subtilis chromosome. Nucleic Acids Res 17:4410). The following PCR conditions were used for PCR A: 2 μM of primer tkt Rec1S (according to SEQ ID No: 27, FIG. 2) and tkt Rec1AS (according to SEQ ID No: 28, FIG. 2), 0.2 mM of each nucleotide (ATP, GTP, TTP, CTP), 2.5 U of a proof-reading DNA polymerase (Stratagene, Gebouw Calif., 1101 CB Amsterdam Zuidoost, The Netherlands), 100 ng of the amplified tkt gene of Example 2 in the appropriate buffer as supplied together with the DNA polymerase.

Temperature regulation was as follows:
Step 1: 3 min at 95° C.
Step 2: 30 sec at 95° C.
Step 3: 30 sec at 52° C.
Step 4: 30 sec at 72° C.
Step 5: 5 min at 72° C.
Steps 2 to 4 were repeated 30-times.

PCR B was done under the following conditions: 2 μM of primer tkt Rec 2S (according to SEQ ID No: 29, FIG. 2) and tkt Rec 2AS (according to SEQ ID No: 30, FIG. 2), 0.2 mM of each nucleotide (ATP, GTP, TTP, CTP), 2.5 U of a proof-reading DNA polymerase (Stratagene, Gebouw Calif., 1101 CB Amsterdam Zuidoost, The Netherlands), 100 ng of the amplified tkt gene of Example 2 in the appropriate buffer as supplied together with the DNA polymerase.

Temperature regulation was as follows:
Step 1: 3 min at 95° C.
Step 2: 30 sec at 95° C.
Step 3: 30 sec at 52° C.
Step 4: 2 min at 72° C.
Step 5: 5 min at 72° C.
Steps 2 to 4 were repeated 30-times.

The two PCR products A and B were purified by Agarose gel electrophoresis and a following extraction out of the gel using the MinElute Gel Extraction Kit from Qiagen (QIAGEN GmbH, QIAGEN Str. 1, 40724 Hilden, Germany). Due to the overlapping regions of the two PCR products A and B with the sequence of the neomycin resistance cassette, it is possible to assemble them by a third PCR: 2 μM of primer tkt Rec 1S and tkt Rec 2AS, 0.2 mM of each nucleotide (ATP, GTP, TTP, CTP), 2.5 U of a proof-reading DNA polymerase (Stratagene, Gebouw Calif., 1101 CB Amsterdam Zuidoost, The Netherlands), 100 ng of PCR product A, 100 ng of PCR product B, and 100 ng of neomycin resistance cassette in the appropriate buffer as supplied together with the DNA polymerase.

Step 1: 3 min at 95° C.
Step 2: 30 sec at 95° C.
Step 3: 30 sec at 55° C.
Step 4: 2.5 min at 72° C.
Step 5: 5 min at 72° C.
Steps 2 to 4 were repeated 35-times.

Five assembling PCRs were pooled and purified with the Qiagen PCR purification Kit (QIAGEN GmbH, QIAGEN Str. 1, 40724 Hilden, Germany) and eluted in 50 μl elution buffer. The correct PCR product was confirmed by agarose gel electrophoresis and used for transformation of B. subtilis PY79. Preparation of competent B. subtilis cells was done according to Kunst et al., 1988 (F. Kunst, M. Debarbouille, T. Msadek, M. Young, C. Mauel, D. Karamata, A. Klier, G. Rapoport, and R. Dedonder. 1988. Deduced polypeptides encoded by the Bacillus subtilis sacU locus share homology with two-component sensor-regulator systems. J Bacteriol 170: 5093-101). 2 ml MNGE+Bacto Casamino Acid (CAA) (9 ml MN-medium (13.6 g/l $K_2HPO_4$, 6.0 g/l $KH_2PO_4$, 0.88 g/l sodium citrate*$2H_2O$), 1 ml glucose (20%), 40 μl potassium glutamate (40%), 50 μl, ammonium iron(III) citrate (2.2 mg/l, freshly prepared), 100 μl tryptophan (8 mg/l), 30 μl $MgSO_4$ (1 M), +/−50 μl Bacto Casamino Acid (20%, Becton Dickinson AG, Postfach, CH-4002 Basel, Switzerland) were inoculated with a single colony and incubated overnight at 37° C. and 250 rpm. This culture was used to inoculate 10 ml MNGE+ CAA (start $OD_{500\,nm}$ of 0.1) and was incubated at 37° C. under shaking (250 rpm) until it reached an $OD_{500\,nm}$ of 1.3. The culture was diluted with the same volume of MNGE w/o CAA and was incubated for another hour. After a centrifugation step (10 min, 4000 rpm, 20° C.), the supernatant was decanted into a sterile tube. The pellet was re-suspended in ⅛ of the kept supernatant. 300 μl of cells were diluted in 1.7 ml MN (1×), 43 μl glucose (20%) and 34 μl $MgSO_4$ (1 M). 10 and 20 μl of the prepared PCR product was added to 400 μl of the diluted competent cells and shaked for 30 min at 37° C. 100 μl expression mix (500 μl 5% yeast extract (Becton Dickinson AG, Postfach, CH-4002 Basel, Switzerland), 125 μl CAA (20%), 1/100 of the final antibiotic concentration (2 μg/ml neomycin), if used for selection, and 750 μl sterile bidest. water) were added and the cells were shaked for 1 h at 37° C. At the end, the cells were spun down, suspended in 200 μl of the supernatant and plated onto TBAB plates (Becton Dickinson AG, Postfach, CH-4002 Basel, Switzerland) containing 2 μg/ml neomycin.

Two transformants were grown in VY medium (5 g/l yeast extract (Becton Dickinson AG, Postfach, CH-4002 Basel, Switzerland), 25 g/l veal infusion broth (Sigma)). From one of the transformants, designated BS3402, the genomic DNA was isolated as described in Example 1 and the correct replacement of the transketolase DNA fragment from base pair 1043 to 1561 by the neomycin gene cassette was confirmed by a standard PCR using tkt Rec 1S and tkt Rec 2AS as primers. As expected for a transketolase deletion mutant, the strain could not grow on ribose or gluconate as sole carbon source and required all three aromatic amino acids or shikimic acid for growth.

Example 5

Transformation of the Transketolase-Deficient *B. subtilis* Strain BS3402 with the Genes of the Transketolase Variants 0.5 and 1 µg DNA of the amplified transketolase gene and its variants (Example 2 and 3) were used to transform BS3402 as described in Example 4. Positive colonies were identified by growth on minimal medium (2 g/l glucose and sorbitol in SMS-medium (2 g/l $(NH_4)_2SO_4$, 14 g/l $K_2HPO_4$, 6 g/l $KH_2PO_4$, 1 g/l tri-sodium citrate, 0.2 g/l $MgSO_4*7H_2O$; 1.5% agar (Becton Dickinson AG, Postfach, CH-4002 Basel, Switzerland) and trace elements (500-times concentrate: 5.0 g/l $MnSO_4 \times 1H_2O$, 2.0 g/l $CoCl_2*6H_2O$, 0.75 g/l $(NH_4)_6Mo_7O_{24}*4H_2O$, 0.5 g/l $AlCl_3*6H_2O$, 0.375 g/l $CuCl*2H_2O$)). Colonies were visible after 24 to 48 h. All transformants were sensitive to neomycin indicating the replacement of the neomycin gene by the introduced wild-type and mutated tkt genes. Genomic DNA was isolated from the transformants and the tkt gene was amplified by PCR as described in Example 1. The introduced mutations were confirmed by sequencing. No further nucleotide exchanges were observed. The generated *B. subtilis* strains were called: R357A-BS3403, R357H-BS3482, R357K-BS3484, R357G-BS3512, R357V-BS3487, R357I-BS3509, R357L-BS3507, R357T-BS3492, R357S-BS3490, R357M-BS3505, R357N-BS3486, R357Q-BS3488.

Example 6

Transduction of *B. subtilis* RB50::[pRF69] (EP 0405 370) with Bacteriophage PBS-1 Lysate of the Transketolase-Deficient Wild-Type Strain BS3402

Transduction work with phage PBS-1 was done as described in Henkin et al., 1984 (Henkin, T. M., and G. H. Chambliss. 1984. Genetic mapping of a mutation causing an alteration in *Bacillus subtilis* ribosomal protein S4. Mol Gen Genet 193:364-9). For preparation of the PBS-1 lysate, the strain BS3402 was grown on TBAB plates (5 µg/ml neomycin) at 37° C. overnight. The cells were used to inoculate 25 ml LB medium (Becton Dickinson AG, Postfach, CH-4002 Basel, Switzerland) to an OD of Klett 20-30 (using the green filter). When 50% of the cells were motile, 0.2 ml of the PBS-1 phage lysate (Henkin, T. M., and G. H. Chambliss. 1984. Genetic mapping of a mutation causing an alteration in *Bacillus subtilis* ribosomal protein S4. Mol Gen Genet 193: 364-9) were added to 0.8 ml of the culture broth. After 30 min incubation at 37° C. under shaking, 9 ml LB-medium were added. This was followed by another 30 min incubation step at 37° C. Then 4 µg/ml chloramphenicol were added, and the incubation was continued for another 2 hours. Finally, the tubes were transferred into a 37° C. dry incubator where they were left overnight. On the next morning, the culture was filtered through a 0.45 µm filter and stored at 4° C. or directly used for transduction.

For the transduction of the riboflavin overproducing strain RB50::[pRF69], the strain was grown on a TBAB plate at 37° C. overnight. Cells of this plate were used to inoculate 25 ml LB-medium (Klett 20-30). When the culture reached Klett 175, 0.8 ml of the cells were mixed with 0.2 ml of a PBS-1 phage lysate from strain BS3402 prepared as described above. After 30 min incubation at 37° C. under shaking, cells were spun down and suspended in 1 ml VY medium. This was followed by 1 h incubation under the identical conditions. 200 to 1000 µl of the transduced cells were plated on a selection plate containing 2 µg/ml neomycin. Grown colonies were tested for neomycin resistance. After gDNA isolation (Example 1), a standard PCR using primer tkt 1S and Rec 2AS was done to confirm the replacement of the tkt wild-type gene by the construct of Example 4. A confirmed strain was called BS3523.

Example 7

Introduction of the Modified Transketolase Genes into Strain BS3523

For preparation of PBS-1 lysates of strains BS3403, BS3482, BS3484, BS3486, BS3490, and BS3512, the respective strains were grown on TBAB plates (5 µg/ml neomycin) overnight at 37° C. Cells from those plates were used to inoculate 25 ml LB medium to an OD of Klett 20-30 (using the green filter). When 50% of the cells were motile (around Klett 150), 0.2 ml of the PBS-1 phage lysate (Henkin, T. M., and G. H. Chambliss. 1984. Genetic mapping of a mutation causing an alteration in *Bacillus subtilis* ribosomal protein S4. Mol Gen Genet 193:364-9) were added to 0.8 ml of the culture broth. After 30 min incubation at 37° C. under slight shaking or turning (roller drum), 9 ml LB-medium were added to the cells. They were incubated for another 30 min under the same conditions. Chloramphenicol was added to a concentration of 4 µg/ml, and the incubation was continued for another 2 hours. The tubes were incubated overnight at 37° C. without shaking. On the next morning, the culture was filtered through a 0.45 µm filter and stored at 4° C. or directly used for subsequent transduction. For this, the transketolase-deficient strain BS3523 (see example 6) was grown on a TBAB plate overnight at 37° C. Cells from the plate were used to inoculate 25 ml LB-medium (Klett 20-30). The culture was incubated at 37° C. under shaking. When the culture reached Klett 175, 0.8 ml of the cells were mixed with 0.2 ml of PBS-1 phage lysate of each of the strains BS3403, BS3482, BS3484, BS3486, BS3490, and BS3512 as described above. After 30 min incubation at 37° C. under shaking, cells were spun down and suspended in 1 ml VY medium. After 1 h incubation under the identical conditions, the cells were spun down again, suspended in 0.2 ml 1×SMS medium and plated onto selection plates (1×SMS as described above with 1 g/l glucose, 1 g/l Sorbitol, and 15% agarose). Grown colonies were tested for loss of neomycin resistance. After gDNA isolation (Example 1), a standard PCR using primer tkt 15 and Rec 2AS was done to amplify the tkt gene from the genomic DNA. The tkt gene of colonies that showed a replacement of the inactivated tkt gene by an intact one, were sequenced to confirm the existence of the mutations. The generated strains were called BS3525 (BS3484 lysate), BS3528 (B53482 lysate), BS3530 (BS3486), BS3534 (BS3403 lysate), BS3535 (BS3490 lysate), BS3541 (BS3512 lysate).

Example 8

Growth of the Transketolase Mutant Strains on Glucose and Gluconate

To evaluate the effect of the transketolase mutations on viability and growth of *B. subtilis*, the maximal growth rate of the generated strains was determined on 2 g/l glucose or gluconate. The following medium was used: 1×SMS (2 g/l (NH$_4$)$_2$SO$_4$, 14 g/l K$_2$HPO$_4$, 6 g/l KH$_2$PO$_4$, 1 g/l tri-sodium citrate, 0.2 g/l MgSO$_4$*7H$_2$O), 2 g/l glucose or gluconate, 500 µg/l yeast extract and trace elements solution as described in Example 5. 25 ml of the described medium in a 300 ml flask with baffles were inoculated from an overnight culture (5 ml VY, resuspended in 1 ml fresh VY) to an OD of Klett 20 to 30. They were incubated at 37° C. under shaking (220 rpm). The OD of the cultures were followed in one hour intervals during the lag phase. During the logarithmic phase the interval was reduced to 30 min. At least four data points during the logarithmic phase were used for the determination of the maximal growth rate.

TABLE 1

| B. subtilis mutant | Growth rate on glucose | % wild type | Growth rate on gluconate | % wild type | ratio |
|---|---|---|---|---|---|
| Wild type PY79 | 0.480 | 100% | 0.351 | 100% | 1.42/1 |
| R357G | 0.384 | 80% | 0.300 | 86% | 1.28/0.93 |
| R357S | 0.372 | 78% | 0.254 | 72% | 1.46/1.08 |
| R357T | 0.342 | 71% | 0.240 | 68% | 1.43/1.04 |
| R357N | 0.366 | 76% | 0.231 | 66% | 1.58/1.15 |
| R357A | 0.381 | 79% | 0.225 | 64% | 1.69/1.23 |
| R357L | 0.324 | 68% | 0.189 | 54% | 1.71/1.25 |
| R357H | 0.324 | 68% | 0.174 | 50% | 1.86/1.36 |
| R357K | 0.348 | 73% | 0.171 | 49% | 2.04/1.48 |
| R357I | 0.243 | 51% | 0.108 | 31% | 2.25/1.65 |
| R357Q | 0.228 | 48% | 0.09 | 26% | 2.53/1.83 |
| R357V | 0.297 | 62% | 0.101 | 24% | 2.94/2.58 |
| R357M | 0.258 | 54% | 0.066 | 19% | 3.91/2.84 |
| R357Y | 0.222 | 46% | 0.06 | 17% | 3.70/2.71 |
| R357F | 0.174 | 36% | 0.038 | 11% | 4.58/3.27 |
| R357D | 0.156 | 33% | 0 | 0% | — |

The wild-type strain PY79 showed as expected the highest growth rate on both substrates. By introducing the different mutations at transketolase position 357, the growth on gluconate was, as expected, much more affected than the growth on glucose. Reduction of the maximal growth rate on gluconate was used as a measurement for the effect of the transketolase mutation on the flux through the non-oxidative pentose phosphate shunt and on the accumulation of the pentose phosphates. A wide range of growth rates were covered by the shown mutations.

Example 9

Riboflavin Production in Shake Flasks 5 ml VY containing chloramphenicol (10 µg/ml) were inoculated with the riboflavin production strains RB50::[pRF69], BS32525, BS3528, BS34530, BS3434, BS34335, and BS3441 (see Example 7). After overnight incubation, the cells were spun down (15 min, 4000 rpm) and suspended in 1 ml screening medium (2×SMS, 10 g/l glucose, 1 g/l yeast extract, and trace elements as described in example 5). A 200 ml flask with baffles containing 25 ml screening medium was inoculated with 0.25 ml of the re-suspended cells. The cultures were incubated for 48 h at 37° C. in a water-saturated atmosphere. After 48 h incubation time, during which the supplied glucose was used up in all of the cultures, a sample of 0.5 ml was taken from the cultures, 35 µl 4 N NaOH was added and the mixture was vortexed for 1 min 465 µl 1 M potassium phosphate buffer, pH 6.8, was added directly afterwards. The mixture was cleared by 5 min centrifugation at 14000 rpm (Eppendorf centrifuge 5415D). The supernatant was transferred into a new tube. Two different methods for riboflavin determination were used. For the calorimetric determination, 200 µl of the supernatant was diluted with 800 µl water. The absorption at 444 nm was multiplied with the factor of 0.03305 to obtain gram riboflavin per liter medium. For the final results, the obtained values were corrected for volume differences. The riboflavin concentration was also determined by HPLC according to Example 10. The results are shown in Table 2:

TABLE 2

| Strain | UV results Riboflavin [mg/l] | % of RB50::[pRF69] | HPLC results (riboflavin [mg/l] | % of RB50::[pRF69] |
|---|---|---|---|---|
| BS3528 (R357H) | 179 | 171% | 139 | 193% |
| BS3535(R357S) | 173 | 166% | 136 | 188% |
| BS3534(R357A) | 144 | 138% | 124 | 172% |
| BS3525(R357K) | 148 | 142% | 112 | 155% |
| BS3559(R357Q) | 134 | 129% | 103 | 143% |
| BS3530(R357N) | 126 | 120% | 93 | 129% |
| RB50::[pRF69] | 104 | 100% | 72 | 100% |
| BS3541(R357G) | 92 | 89% | 66 | 92% |
| BS3523(deletion) | 90 | 87% | 58 | 81% |

Nearly all Bacillus strains containing a transketolase mutation showed a clearly increased riboflavin production, while the transketolase negative strain produced less riboflavin than to the control strain. In the case of the R357H mutation, the riboflavin concentration was nearly doubled.

Example 10

Riboflavin Fermentation

Fermentation runs were performed as described in EP 405370.
Fermentations were run with strains (1) RB50::[pRF69], (2) BS3534 (R357A), and (3) BS3528 (R357H). At 24 hours and 48 hours fermentation time, concentrations of riboflavin and biomass (cell dry weight) were measured in the culture broth. As shown in Table 3, parent strain RB50::[pRF69] produced 9.8 g/l riboflavin in 48 h with a yield on substrate of 3.59% (w/w). Biomass was produced with a yield on substrate of 20.3% (w/w). Derivatives of RB50::[pRF69] expressing a modified transketolase gene showed significant increases in riboflavin production. BS3528 and BS3534 produced 11.7 g/l and 14.6 g/l, respectively. This corresponds to a yield on glucose of 4.23% with BS3528 and 5.14% with BS3534, respectively (Table 3). These results demonstrate that the modification of transketolase activity leads to an increase in riboflavin productivity.

TABLE 3

Riboflavin and biomass yield on substrate after 48 h fermentation time

| | B2 Yield [%] (w/w) | Difference | Biomass Yield [%] (w/w) | Difference |
|---|---|---|---|---|
| RB50::[pRF69] | 3.59 ± 0.27 | | 20.26 ± 0.80 | |
| BS3534 | 5.14 ± 0.09 | +43% | 18.92 ± 0.37 | −7% |
| BS3528 | 4.23 ± 0.19 | +18% | 17.78 ± 1.73 | −12% |

Example 11

Analytical Methods for Determination of Riboflavin

For determination of riboflavin, the following analytical method can be used (Bretzel et al., J. Ind. Microbiol. Biotechnol. 22, 19-26, 1999).

The chromatographic system was a Hewlett-Packard 1100 System equipped with a binary pump, a column thermostat and a cooled auto sampler. Both a diode array detector and a fluorescence detector were used in line. Two signals were recorded, UV at 280 nm and fluorescence trace at excitation 446 nm, emission 520 nm.

A stainless-steel Supercosil LC-8-DB column (150×4.6 mm, 3 μm particle size) was used, together with a guard cartridge. The mobile phases were 100 mM acetic acid (A) and methanol (B). A gradient elution according to the following scheme was used:

| Time [min] | % A | % B |
|---|---|---|
| 0 | 98 | 2 |
| 6 | 98 | 2 |

-continued

| Time [min] | % A | % B |
|---|---|---|
| 15 | 50 | 50 |
| 25 | 50 | 50 |

The column temperature was set to 20° C., and the flow rate was 1.0 ml/min. The run time was 25 min.

Fermentation samples were diluted, filtered and analyzed without further treatment. Riboflavin was quantitated by comparison with an external standard. The calculations were to based on the UV signal at 280 nm. Riboflavin purchased from Fluka (9471 Buchs, Switzerland) was used as standard material (purity ≥99.0%).

The invention claimed is:

1. A modified transketolase originated from *Bacillus* or *Corynebacterium*, wherein the amino acid sequence of the modified transketolase contains at least one mutation, so that the specific activity of the modified enzyme is reduced in comparison to the corresponding non-modified wild-type enzyme, said at least one mutation leading to a reduced activity of between 10 to 90% towards metabolism of carbon sources that are exclusively metabolized by the pentose phosphate pathway compared to the activity of the respective non-modified wild-type enzyme.

2. A recombinant host cell comprising the modified transketolase according to claim 1, wherein the growth rate on a carbon source that is exclusively metabolized by the pentose phosphate pathway is reduced to between 10 to 90% in comparison to the growth rate of the respective host cell containing the wild-type transketolase.

3. A modified transketolase used in a process for producing riboflavin, wherein at least one mutation is introduced such that, in the process for producing riboflavin, after replacing the wild-type transketolase(s) of a riboflavin-producing host cell with the modified one, the growth rate of the generated new strain on a carbon source that is metabolized exclusively by the pentose phosphate pathway is reduced in comparison to the growth rate of the original host cell containing the wild-type transketolase to a growth rate of between 10 to 90% in comparison to the host cell containing the wild-type transketolase.

4. A process for the production of a substance for which ribose-5-phosphate, ribulose-5-phosphate, or xylulose-5-phosphate is a biosynthetic precursor comprising:
   a) culturing the recombinant host cell of claim 2 in fermentation medium, wherein the substance is produced; and
   b) separating the substance from the medium.

5. The process according to claim 4, wherein as the substance riboflavin, a riboflavin precursor, FMN, FAD, pyridoxal phosphate or one or more derivatives thereof is/are produced.

6. The process according to claim 5, wherein riboflavin or derivatives thereof are produced.

* * * * *